US006692702B1

(12) United States Patent
Burshteyn et al.

(10) Patent No.: US 6,692,702 B1
(45) Date of Patent: Feb. 17, 2004

(54) APPARATUS FOR BIOLOGICAL SAMPLE PREPARATION AND ANALYSIS

(75) Inventors: Alexander Burshteyn, Hialeah, FL (US); John W. Joubran, Miami, FL (US); Nazle Kuylen, Miami, FL (US); Frank J. Lucas, Boca Raton, FL (US)

(73) Assignee: Coulter International Corp., Miami, FL (US)

( * ) Notice: Subject to any disclaimer, the term of this patent is extended or adjusted under 35 U.S.C. 154(b) by 304 days.

(21) Appl. No.: 09/611,847

(22) Filed: Jul. 7, 2000

(51) Int. Cl.[7] .................................................. G01N 1/34
(52) U.S. Cl. ................. 422/101; 422/82.01; 422/82.02; 436/63; 436/178; 435/308.1; 210/416.1
(58) Field of Search ............................. 422/101, 82.08, 422/82.01; 436/63, 178; 435/308.1; 210/398, 416.1, 433.1, 442, 500.23

(56) References Cited

U.S. PATENT DOCUMENTS

| | | | |
|---|---|---|---|
| 4,680,025 A | 7/1987 | Kruger et al. | |
| 4,755,300 A | 7/1988 | Fischel et al. | |
| 4,776,964 A | 10/1988 | Schoendorfer et al. | |
| 4,808,307 A | 2/1989 | Fischel et al. | |
| 4,846,786 A | 7/1989 | Freed et al. | |
| 4,851,126 A | 7/1989 | Schoendorfer | |
| 4,871,462 A | 10/1989 | Fischel et al. | |
| 4,944,883 A | 7/1990 | Schoendorfer et al. | |
| 4,968,600 A | 11/1990 | Haraguchi et al. | |
| 5,034,135 A | 7/1991 | Fischel | |
| 5,149,661 A | 9/1992 | Gjerde et al. | |
| 5,190,657 A | 3/1993 | Heagle et al. | |
| 5,192,439 A | 3/1993 | Roth et al. | |
| 5,240,856 A | * 8/1993 | Goffe et al. | |
| 5,258,127 A | 11/1993 | Gsell et al. | |
| 5,288,403 A | 2/1994 | Ohno | |
| 5,290,449 A | 3/1994 | Heagle et al. | |
| 5,362,406 A | 11/1994 | Gsell et al. | |
| 5,454,946 A | 10/1995 | Heagle et al. | |
| 5,601,727 A | * 2/1997 | Bormann et al. | |
| 5,674,173 A | 10/1997 | Hlavinka et al. | |
| 5,686,238 A | 11/1997 | Martinson et al. | |
| 5,695,989 A | * 12/1997 | Kalamasz | |
| 5,711,871 A | 1/1998 | Miltenyi | |
| 5,744,047 A | 4/1998 | Gsell et al. | |
| 5,753,014 A | 5/1998 | Van Rijn | |
| 5,785,869 A | 7/1998 | Martinson et al. | |
| 5,798,221 A | 8/1998 | AEgidius | |
| 5,811,061 A | 9/1998 | Martinson et al. | |
| 6,068,775 A | 5/2000 | Custer et al. | |
| 6,153,442 A | 11/2000 | Pirio et al. | |

FOREIGN PATENT DOCUMENTS

WO     WO 96/04067     2/1996

OTHER PUBLICATIONS

Legallais, et al, "Strategies for the depyrogenation of contaminated immunoglobulin G solutions by histidine–immobilized hollow fiber membrane", *Journal of Chromatography B*, Elsevier Science B.V., 691 (1997), pp. 33–41.

A/G Technology Corporation "(UF/MF) Operating Guide", (OG1/99R2), Jan. 1999.

"Flow Cytometry and Sorting", Melamed, et al., New York: Wiley–Liss, Inc. (2nd ed., 1990).

Shapiro, H.M., "Practical Flow Cytometry", New York: Wiley–Liss, Inc. (3rd ed., 1995).

* cited by examiner

*Primary Examiner*—Jan Ludlow
(74) *Attorney, Agent, or Firm*—Howson and Howson; Mitchell E. Alter

(57) ABSTRACT

A method for utilizing a filtration device for removing interferants from a sample containing cells in an automated apparatus is disclosed. The filtration device includes a microporous hollow fiber membrane having a plurality of pores sized to retain cells while allowing smaller diameter interferants to pass through the membrane. The apparatus also includes a means for of moving the sample from a sample container to and from the filtration device. The disclosed method utilizes a vacuum source to aspirate the sample into a lumen of the hollow fiber membrane so that the sample is retained in the lumen space until expelled into an analysis container or transported to an analyzer.

14 Claims, 24 Drawing Sheets

| First Step 80 - Applying a vacuum force to a blood cell sample to cause the blood cell sample contact a filter |
|---|
| Second Step 82 - Applying a force to the blood cell sample in contact with the filter, whereby interferants in the blood cell sample pass through the filter while the cells in the blood cell sample do not pass through the filter |
| Third Step 84 - Recovering the cells from the filter. |

FIG. 5

First Step 90- Adding a probe that binds the phenotypic market to the sample of cells to be analyzed to form a test sample mixture Second Step 92 - Applying a vacuum force to a blood cell sample to cause the blood cell sample contact a filter Third Step 94 - Applying a force to the blood cell sample in contact with the filter, whereby interferants in the blood cell sample pass through the filter while the cells in the blood cell sample do not pass through the filter Fourth Step 96 - Recovering the cells from the filter.

FIG. 6

APPARATUS FOR BIOLOGICAL SAMPLE PREPARATION AND ANALYSIS

FIELD OF THE INVENTION

The invention relates generally to the field of biological sample preparation and analysis. More particularly, the subject invention relates to a method and apparatus for enhancing the sensitivity of blood cell analysis.

BACKGROUND OF THE INVENTION

Flow cytometry is a well known technique for qualitatively and quantitatively analyzing a large number of individual cells for a specific cellular marker in a rapid manner. In a typical application, a fluorescent molecular probe that selectively binds to a predetermined cell marker, such as a fluorochrome-conjugated antibody that specifically binds an intracellular or cell surface antigen, is added to a cell sample to be analyzed so that the probe can bind or "stain" the cells within the sample that express the predetermined cell marker. The sample is then placed in flow cytometer and illuminated with a light source to enable the fluorescence associated with each cell in the sample to be quantified. The magnitude of fluorescence emitted from a particular cell correlates with the quantity of cell marker on or in that particular cell. By extrapolating this fluorescence data, the relative quantity of specific phenotypic markers expressed by cells in a sample can be rapidly and accurately determined. For an overview of flow cytometric analysis see, "Flow Cytometry and Sorting," Myron R. Melamed, Tore Lindmo, and Mortimer L. Mendelsohn, eds., New York: Wiley-Liss, Inc., (3rd ed., 1995); Shapiro, H. M., "Practical Flow Cytometry," New York: Wiley-Liss, Inc., (2nd ed., 1990).

Sample preparation for flow cytometric analysis is typically performed in a non-automated fashion, wherein a saturating concentration of a cell marker-specific probe is added to a cell sample by manual pipetting, and the mixture is then incubated for a period of time sufficient to allow the probe to bind the cell marker of interest. For analyses where red blood cells might cause interference (e.g., immunophenotyping leukocytes), the red blood cells can be removed from the sample using an agent that specifically lyses erythrocytes (for example, a hypotonic solution, ammonium chloride or carboxylic acid). Traditionally, to remove interfering unbound probe from the cell sample prior to flow cytometric analysis, the mixture is washed by adding excess buffer to the mixture, centrifuging the mixture to separate the cells from the buffer, removing the buffer containing the unbound probe, and resuspending the cells in fresh buffer. The washing procedure can be repeated multiple times to further remove any remaining unbound probe. This non-automated technique is advantageous in that it results in a relatively clean sample that contains few interferants (for example, unbound probe or cell debris) which might generate background noise or interference during the flow cytometric analysis. For many applications, however, this non-automated technique is relatively time-consuming, can result in significant cell loss due to one or more wash steps, and exposes the cells to the potentially deleterious effects (for example, activation of enzymatic processes, granule release, cell destruction, high gravity forces produced by centrifugation, etc).

While the foregoing technique is acceptable for infrequent analyses involving a small number of samples, it is less suitable for protocols involving repeated analyses of a large number of samples. A more automated procedure is generally preferred when flow cytometric analysis is employed for clinical diagnostics, high-throughput screening, or the like. For example, in a typical clinical assay where leukocytes are immunophenotyped using flow cytometry, a sample of whole blood is placed into an apparatus that automatically processes the sample prior to analysis. One such apparatus is the COULTER® TQ-Prep™ Workstation system manufactured by Beckman Coulter, Inc. (Miami, Fla.). After adding a probe to the sample, this apparatus uses computer-controlled devices to automatically add an agent that lyses erythrocytes in the sample and a cell fixing agent (for example, paraformaldehyde). The prepared sample can then be analyzed using a flow cytometer without further processing. This automated technique is advantageous in that samples of whole blood can be prepared for analysis quickly and efficiently.

A drawback of this lysing technique can be encountered in applications requiring a high degree of sensitivity. In such applications, in the absence of a washing step, the automated technique does not remove interferants, such as unbound probe or debris from the lysed erythrocytes from the sample. The high background signal caused by the fluorescence from the unbound probe, non-specific probe binding, and/or autofluorescence from the cells and debris can obscure results generated from the analysis.

Where a fluorescently-labeled antibody is used to analyze a cell sample for a marker present in low quantities, the absence of a washing step can result in high background fluorescence caused by the unbound antibody present in the sample. Thus, if too many unbound fluorescent antibody molecules are present in the sample, the flow cytometer can not distinguish the signal emitted from the antibody-bound cells from the "noise" generated by the unbound antibody. That is, the "noise" in the sample overwhelms the "signal" emanating from the cells of interest. To avoid this, the signal to noise ratio in the sample can be improved by removing the interferants by manually washing. An example of manual washing comprises centrifuging the sample to pellet the cells, decanting the interferants contained in the supernatant, and resuspending the cells in fresh buffer. As described above for the non-automated technique, this manual washing is disadvantageous because it is time consuming, causes cell damage, and can result in significant cell loss.

A need therefore exists for an apparatus and method for quickly and efficiently removing interferants from a cell sample prior to analysis. In addition, the apparatus and method should minimize the risk of exposure to infectious blood because of operator handling of the blood cell sample. An apparatus that performs the foregoing method with only negligible cell loss, and does not expose cells to high gravitational forces or cell packing caused by centrifugation would be especially advantageous.

SUMMARY OF THE INVENTION

It has been discovered that filters, such as microporous hollow fiber membranes, can be utilized in cell sample preparation devices to quickly and efficiently remove interferants from a cell sample. More specifically, it has been found that the use of a hollow fiber membrane having a plurality of pores with a mean diameter less than the diameter of the cells of interest can be utilized to remove interferants from a cell sample to improve the signal-to-noise ratio in a cellular assay. Application of vacuum to the hollow fiber membrane permits interferants to be removed from a blood cell sample within a lumen of the filter with little or no cell damage. As the cells themselves do not pass through pores of the membrane, compared with conventional continuous filtration devices, clogging of the filter is less frequent, and cells are exposed to less deleterious forces. Filters within the invention can be installed in a cell processing apparatus such that a blood cell sample can be washed and analyzed automatically.

Accordingly the invention features an apparatus for automatically removing interferants from a sample containing cells. The apparatus includes a vacuum source; a filtration device comprising an impermeable housing that forms an extramembrane chamber wherein said chamber contains a filter that selective retains cells of interest while allowing interferants to pass through the filter, and wherein said housing contains at least three port and wherein at least one port is connected by a conduit to the vacuum source; a conduit from one of said ports in said housing which is adapted to aspirate a cell sample from a sample container into the filtration device by said vacuum source; and a conduit from one of said ports in said housing which fluidly connects to a buffer reservoir, which provides a means for buffer to enter into said filtration device to recover the retained cells through one of said ports.

In a preferred embodiment, the apparatus for automatically removing interferants from a sample containing cells includes a sample container holder adapted for holding a sample container containing the sample of cells; a filtration device comprising a filter that selectively retains the cells while allowing the interferants to pass therethrough; at least one conduit fluidly connecting the sample container to the filtration device whereby the sample can move between the sample container and the filtration device; and a means for recovering the cells from the filtration device. The filter of the apparatus preferably includes a microporous hollow fiber membrane having a plurality of pores sized such that cells are prevented from passing therethrough. For example, the pores can have a mean diameter of between about 0.1 and 5.0 microns. In preferred versions of the apparatus, the microporous hollow fiber membrane is fashioned into at least one tube defining a lumen, the tube having a first port providing a first opening in the tube, and a second port providing a second opening in the tube. In this preferred embodiment, the conduit can be fluidly connected to the at least one lumen via the first port such that the cell sample can be moved from the cell sample container through the first port into the at least one lumen. The second port can be fluidly connected to a buffer reservoir containing a buffer and also fluidly connected to a detergent solution reservoir containing a detergent solution. The means for recovering the cells from the filtration device can include a fluid pump that can be in fluid communication with a buffer reservoir suitable for housing a buffer so that the fluid pump can cause the buffer to flow from the buffer reservoir into the filtration device. In variations, the fluid pump can also cause the buffer to flow from the filtration device into the at least one conduit.

In another aspect of the apparatus of the invention, the filtration device can also include an impermeable housing that forms an extramembrane chamber between the impermeable housing and the microporous hollow fiber membrane. A vacuum source can be fluidly connected to the extramembrane chamber such that application of a vacuum from the vacuum source to the extramembrane chamber causes the sample of cells to be aspirated from the cell sample container through the at least one conduit into at least one lumen of the microporous hollow fiber membrane via the first port, and a portion of the sample of cells to flow through the microporous hollow fiber membrane into the extramembrane chamber.

The apparatus can also include one or more pumps and a plurality of valves. The pumps provide a hydraulic force for transporting the buffer from the buffer reservoir into the lumens of the microporous hollow fiber membrane, and the detergent solution from the detergent solution reservoir into the lumens of the microporous hollow fiber membrane; and the plurality of valves being adapted to open and close such that the vacuum from the vacuum source can be applied to the extramembrane chamber such that the buffer, the detergent solution, and portions of the sample of cells within the lumens of the microporous hollow fiber can be controllably aspirated from the lumens to the extramembrane chamber; and the hydraulic force provided from the pumps can be directed to transport the buffer from the buffer reservoir to the lumens, the buffer from the buffer reservoir to the cell sample container, and the detergent solution from the detergent solution reservoir to the lumens. In another aspect, the apparatus of the invention can include a computer controller for controlling the pumps and valves.

The invention also features a cell analyzing apparatus that includes both a cell washer for removing interferants from a sample of cells and a cell analyzer for analyzing the sample of cells. The cell washer is describe above and the cell analyzer can be any cell analyzers. Preferably the cell analyzer measures fluorescence, such as a flow cytometer.

Also within the invention is an automated method for removing interferants from a sample containing cells. This method includes the steps of applying a vacuum force to a blood cell sample in a first sample container to cause the blood cell sample to contact a filter; applying a force to the blood cell sample in contact with the filter, whereby interferants in the blood cell sample pass through the filter while the cells in the blood cell sample do not pass through the filter; and recovering the cells from the filter. In this method, the filter can include a microporous hollow fiber membrane having a plurality of pores sized such that the cells are prevented from passing therethrough.

The invention also features an automated method of analyzing a phenotypic marker on cells within a sample. This method includes the steps of adding at least one reagent that reacts with blood cells to a blood cell sample to form a test sample mixture; automatically removing interferants from the test sample mixture to yield a washed blood cell sample; and analyzing the washed blood cell sample to determine characteristics of the blood cells. The at least one reagent can be an antibody that specifically binds the phenotypic marker and the antibody can include a fluorescent test label. The step of automatically removing interferants from the test sample mixture can remove greater then 50% of the interferants from the test sample mixture.

The method can also further include the step of lysing erythrocytes in the sample of cells to be analyzed, and/or the step of quantifying the amount of probe bound to the cells in the test sample mixture by use of a flow cytometer.

BRIEF DESCRIPTION OF THE DRAWINGS

FIGS. 4A–4K are schematic views illustrating the operation of an apparatus of the invention.

FIG. 5 is an outline of a method of the invention.

FIG. 6 is an outline of another method of the invention.

DETAILED DESCRIPTION OF THE INVENTION

The below described preferred embodiments illustrate various adaptations of the invention. Nonetheless, from the description of these embodiments, other aspects of the invention can be readily fashioned by making slight adjustments or modifications to the components and steps discussed below.

All publications, patent applications, patents, and other references mentioned herein are incorporated by reference in their entirety. In the case of conflict, the present specification, including definitions will control. In addition, the particular embodiments discussed below are illustrative only and not intended to be limiting.

Unless otherwise defined, all technical terms used herein have the same meaning as commonly understood by one of ordinary skill in the art to which this invention belongs.

The invention provides an automatic apparatus and automatic method utilizing a filter to remove interferants from a body fluid prior to analysis. As used herein the term "automatic" means performed without direct human intervention. For example, an automatic apparatus automatically performs a method when a component of the apparatus, rather than a human operator, performs one or more steps of the method, even though a human operator might input instructions into the machine or even perform one of the steps manually. Similarly, an "automated" method is a method performed automatically. The term "interferants" means substances or particles that obscure an analysis. More specifically, the interferants comprise non-reacted chemical agents; non-reacted biological agents; and biological particles, such as red blood cell debris and cellular matter smaller than the cellular matter of interest. Interferants in a cell sample analyzed fluorescently typically include unbound fluorescent probe and autofluorescent cell debris. A particular percentage of interferants is removed from a sample when either (a) the amount of debris in the sample is decreased by that percentage or (b) the signal to noise ratio is improved by that percentage.

Figure 1:
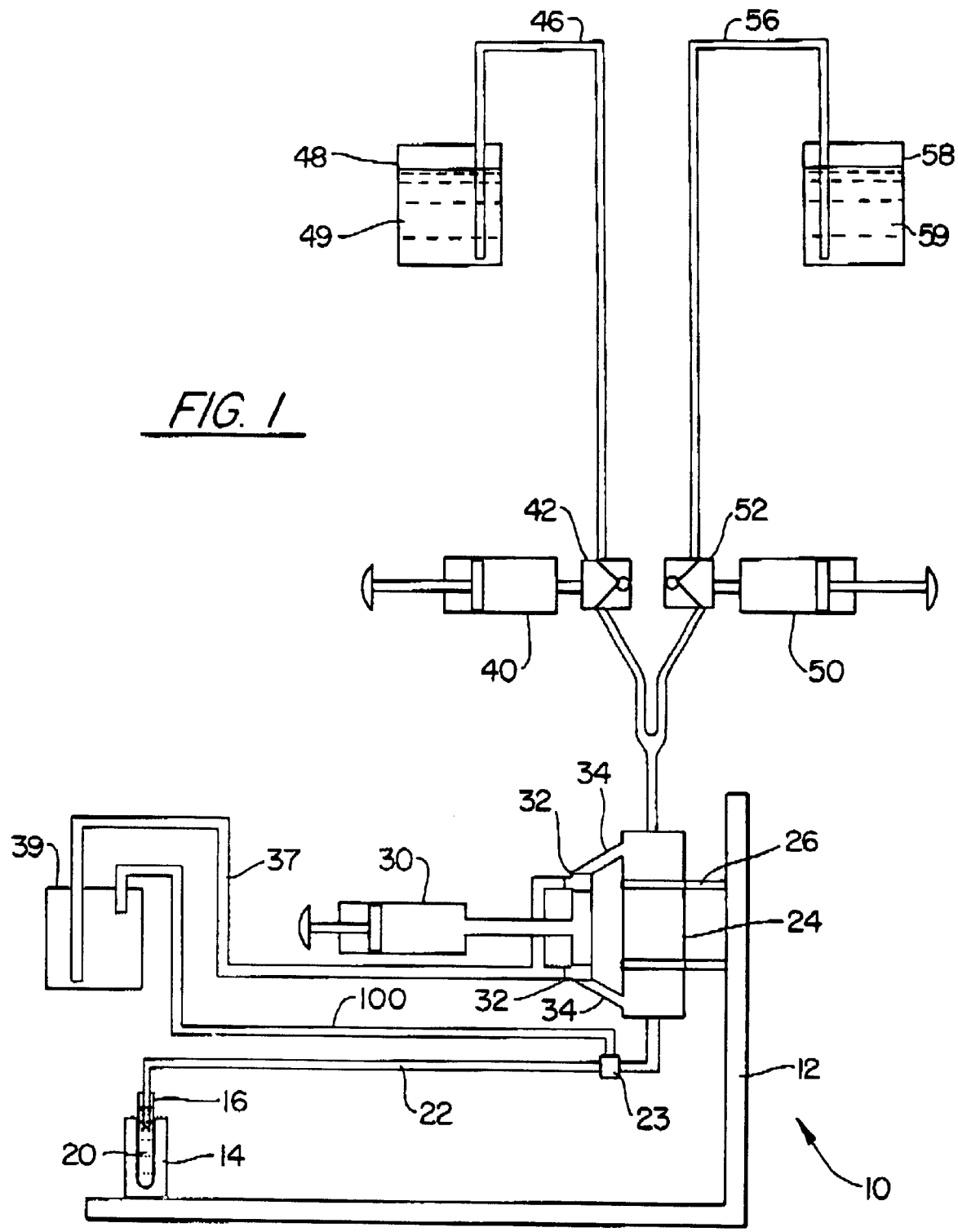
FIG. 1 is a schematic view of an apparatus within the invention.

Referring to FIG. 1 of the drawings, a presently preferred embodiment of a cell wash apparatus 10 includes a sample container holder 14 and a filtration device 24 mounted to a frame 12. Sample container holder 14 accommodates a sample container 16 containing a sample of cells 20 in an arrangement such that an end of a sample hose 22 can be inserted into the sample of cells 20 which can contain interferants. Sample hose 22 is fluidly connected to vacuum source 30 so that actuation of vacuum source 30 supplies a vacuum force which aspirates the sample of cells 20 from sample container 16 into hose 22. More specifically, there is an absence of air in filtration device 24 such that when vacuum force 30 is applied, the cell sample 20 is aspirated from the sample container 16 into the filtration device 24.

Vacuum source 30 can take the form of any device that can provide a vacuum or hydraulic force for moving fluids. For example, vacuum source 30 can be a fluid pump or an external vacuum line. Preferably, the vacuum source 30 is a syringe pump, for example a 5 ml syringe pump, that can provide a vacuum to filtration device 24 when its plunger is withdrawn and a forward hydraulic force when its plunger is depressed.

Devices that cause a vacuum force rather than a positive pressure are the preferred form of source 30, because it has been found that a vacuum is less damaging to cells. More specifically, the sample of blood cells 20 does not circulate through a pump to enter into the lumen 66 (not shown). If the cells circulate through a pump, then cell deformation, aggregation and deterioration occur. Therefore, the sample of cells 20 enter the lumen 66 by action of a vacuum force rather than by the action of a force which is applied to the sample of blood cells 20 which cause the sample of cells 20 to be pushed into the lumen 66.

Filtration device 24 is attached to frame 12 by a filtration device fastener 26 and interposed between sample hose 22 and vacuum source 30 so that application of a vacuum by vacuum source 30 causes aspiration of sample of cells 20 into filtration device 24. Filtration device 24 can be any device that can remove interferants such as unbound antibody molecules or cellular debris from sample of cells 20. In a preferred embodiment, filtration device 24 includes a filter through which interferants can pass. Filters that can be used include fine mesh screens, flat microfiltration membranes, spiral wound membrane cartridges, or any other media that can separate interferants from the cells of interest. In a more preferred embodiment, the filter is a microporous hollow fiber membrane that has a plurality of pores sized less than the blood cells within sample of cells 20 but greater than the interferants.

Suitable hollow fiber membranes for use as filtration device 24 can be fashioned by one of skill in the art or can be purchased from a variety of commercial sources. Hollow fiber membranes useful in the invention comprise a material which is non reactive with the cells of interest and can be a hydrophobic or hydrophilic material, polysulfone, polyestersulfone, nylon, methylacrylates, Peek™ (Upchurch Scientific, Inc.). The filter will have pores sized so that cells of interest cannot pass therethrough. The pore size will range from approximately 0.1 microns to about 5 microns in diameter. Preferably, the pore size will range from approximately 0.1 microns to about 3 microns, which can eliminate platelets as interferants from the cells of interest. More preferably, the pore size will range from approximately 0.2 microns to about 2 microns and most preferably the pore size will range from approximately 0.3 microns to about 1 micron. In the present invention, a pore size of about 0.65 microns has been successfully used to eliminate interferants leaving a majority of cellular components for analysis. One preferred commercially available polysulfone hollow fiber membrane device having a plurality of pores with a mean diameter of 0.65 microns is sold as Catalog# CFP-6-D-H22LA by A/G Technology Corporation (Needham, Mass.). This device is suitable for removing the majority of interferants from a typical sample of 100 microliter of whole human blood that has been stained with a fluorescent antibody, erythrocyte-lysed, and diluted to a total volume of about 4 ml using an isotonic buffer or reagent. Other devices useful for variations of the invention include CFP-6-D-MB01 (15 $cm^2$), and CFP-6-D-MM01A (24 $cm^2$) from A/G Technology Corporation; and X15E300 04N and X25E201 02N from Spectrum Laboratories, Inc. (Rancho Dominguez, Calif.).

A sample hose valve 23 for regulating fluid flow between sample container 16 and filtration device 24 is positioned on hose 22. Valve 23 can take the form of any device that can control the flow of fluid through hose 22. Preferably, valve 23 is switchable between an open position and a closed position. In the open position, sample 20 can flow between container 16 and filtration device 24 when a suitable force is applied, such as by vacuum source 30. In the closed position, the fluid connection is blocked so that sample 20 cannot flow between container 16 and filtration device 24. In a preferred variation of the foregoing, valve 23 also has a partially open position that directs fluid flow from hose 22 to a waste reservoir 39 by another fluid connection.

Although in the embodiment shown in FIG. 1 the fluid connection between sample container 16 and filtration device 24 is provided by sample hose 22 and regulated by valve 23, in an alternate preferred embodiment, more than one fluid connection can exist between sample container 16 and filtration device 24. For example, sample hose 22 can be utilized for transporting sample of cells 20 from container 16 to filtration device 24 and a return hose or fluid connector can be provided for returning sample of cells 20 from device 24 to sample container 16. A fluid flow regulator analogous to valve 23 can be interposed in the return hose. In addition, rather than having a fluid connection for returning sample 20 from device 24 to sample container 16, the apparatus can feature another pathway for transporting sample 20 from device 24 to a clean sample container, such as an unused test tube, rather than sample container 16.

Referring again to FIG. 1, vacuum source valves 32 are positioned within the fluid connection between vacuum source 30 and filtration device 24 so that they can control transfer of vacuum between vacuum source 30 and filtration device 24. Valves 32 are preferably switchable between an open and a closed position. In the open position, actuation of vacuum source 30 causes a vacuum force to be applied to filtration device 24. The vacuum will cause aspiration of sample 20 from container 16 into device 24. In the closed position, no force is transmitted between vacuum source 30 and device 24.

Vacuum source 30 can also be fluidly connected to a waste reservoir 39 by a waste hose 37. As indicated above, vacuum source 30 is also adapted to provide a forward hydraulic force. This hydraulic force can be used to move fluid from locations proximal to vacuum source 30 to waste reservoir 39. For example, when vacuum source 30 takes the preferred form of a syringe pump, with valves 32 and 23 open, withdrawal of the plunger of the syringe pump causes a vacuum that aspirates a liquid which contains interferants and sample of cells 20 to be dispersed into the interior of the syringe's barrel. Depressing the plunger at this point forcibly expels the liquid from the syringe. With valves 32 closed, the liquid is directed through waste hose 37 into waste reservoir 39. In an alternative variation of the foregoing, rather than using vacuum source 30, an additional vacuum source, pump, or hydraulic force transducer can be utilized to move fluid from locations proximal to vacuum source 30 to waste reservoir 39. This latter variation is preferred where it is desired to avoid potential cross contamination between waste reservoir 39 and sample container 16 and their associated fluid connections.

Filtration device 24 can also be fluidly connected to buffer reservoir 48 by buffer hose 46. Buffer reservoir 48 is a container for housing buffer 49 which can be any isotonic solution compatible with sample of cells 20. Suitable buffers include physiological saline or phosphate buffered saline (PBS) and Hanks Buffer. Preferred isotonic solutions for use as buffer 49 include IsoFlow™ buffer, PBS, and IMMUNOTROL™ Final Storage buffer (all available from Beckman Coulter, Inc., Fullerton, Calif.).

Interposed between device 24 and reservoir 48, and fluidly communicating with hose 46 is buffer pump 40. Buffer pump 40 supplies an hydraulic force which moves buffer 49 from reservoir 48 through hose 46, filtration device 24, and sample hose 22 into sample container 16. Pump 40 can take the form of any device that can cause a hydraulic force between buffer reservoir 48, device 24, and sample container 16. For example it can be a vacuum pump, peristaltic pump, reciprocating pump, or other type of pump known to those skilled in the art. In preferred embodiments, however, it is a syringe pump.

Positioned on hose 46 between reservoir 48 and device 24 is a buffer valve 42 for controlling flow of buffer between reservoir 48 and device 24. Although it can be any fluid flow regulating device, valve 42 is preferably a three position stopcock-like valve that can be placed in either a fill position, a dispense position, or a closed position. In the fill position, pump 40 is in fluid connection with buffer reservoir 48 such that it can transmit an hydraulic force to hose 46 that causes pump 40 to aspirate buffer 49 from buffer reservoir 48 into buffer hose 46 or into the chamber of the syringe when pump 40 is a syringe pump. In the dispense position, pump 40 is in fluid communication with device 24 such that actuation of pump 40, for example depressing the plunger of the syringe, causes buffer 49 to be transported from pump 40 to device 24 and, where valve 23 is open, into sample container 16. Thus, referring to FIG. 1, with valve 42 in the open position, valves 32 in the closed position and valve 23 in the open position, actuation of pump 40 can cause buffer 49 to flush sample of blood cells 20 positioned within filtration device 24 back into sample container 16. With valve 42 in the closed position, the fluid connection between reservoir 48, device 24, and container 16 is blocked.

Detergent solution reservoir 58 is fluidly connected to filtration device 24 by detergent solution hose 56. Detergent solution reservoir 58 is a container for housing a detergent solution 59 which is suitable for cleaning filtration device 24 and the fluid connections of apparatus 10. Detergent solution 59 can be any solution that can remove residual samples, accumulated deposits, proteins, nucleic acids and the like from the fluid connections of apparatus 10. For example, detergent solution can be 0.5N NaOH solution, 1N KOH solution, $H_3PO_4$ solution, 0.05–10% bleach solution, or a similar solution. The detergent solution can include substances such as Triton X-100 (Rohm and Haas), Tween 80® (ICI America), pluronic acids (BASF Corp.), ethylenediamine tetraacetic acid (EDTA), proteases, nucleases, azide, and other substances which can clean fluid connections. One preferred composition for use as detergent solution 59 is the solution sold under the trade name COULTER CLENZ® (Beckman Coulter Inc., Fullerton, Calif.).

Detergent solution pump 50 supplies a hydraulic force which moves detergent solution 59 from reservoir 58 through hose 56 into filtration device 24. Similar to pump 40, pump 50 can take the form of any device that can cause an hydraulic force between detergent solution reservoir 58 and device 24. For example it can be a vacuum pump, peristaltic pump, reciprocating pump or other type of pump known to those skilled in the art. In preferred embodiments, however, it is a syringe pump.

Positioned on hose 56 between detergent solution pump 50 and buffer hose 56 is a detergent solution valve 52 for controlling flow of detergent solution 59 between reservoir 58 and device 24. As with valve 42, although it can be any suitable fluid flow regulating device, valve 52 is preferably a three position stopcock-like valve that can be placed in either a fill position, a dispense position, or a closed position. In the fill position, detergent solution pump 50 is in fluid connection with detergent solution reservoir 58 such that it can transmit a hydraulic force to hose 56 that causes pump 50 to aspirate detergent solution 59 from detergent solution reservoir 58 into detergent hose 56 or into the chamber of the syringe when pump 50 is a syringe pump. In the dispense position, pump 50 is in fluid communication with device 24 such that when valve 32 is closed and valve 23 is open, actuation of pump 50, for example depressing the plunger of the syringe, causes detergent solution 59 to be transported from pump 50 to device 24. And when valves 32 are in the open position and valve 23 in the closed position, actuation of pump 50, with or without the cooperation of vacuum source 30, can cause detergent solution 59 to wash any fluid or material within filtration device 24 into waste reservoir 39. With valve 52 in the closed position, the fluid connection between reservoir 58 and device 24 is blocked.

In addition to the above-described buffer and detergent solution devices, other devices can be included within apparatus 10. For example, devices for adding an erythrocyte lysing agent can be included. Similarly, devices for adding one or more cell marker probes, such as fluorescently-labeled antigen-specific antibodies, can be included within apparatus 10. In addition, fluid connections to one or more cell analyzers, such as hematology and flow cytometry analyzers, can also be provided. Thus, the invention can include an apparatus that can automatically process a sample of whole blood by lysing the red blood cells within the blood cell sample, adding a cell marker probe to the blood cell sample, removing the lysed red blood cell debris and unbound cell marker probe from the blood cell sample, and quantifying the remaining cells and quantifying specific cell markers using a cell analyzer.

In a preferred embodiment, the various components of the apparatus are controlled by an information processing unit, such as a computer. That is valves 23, 32, 42, and 52, and vacuum source 30 and pumps 40 and 50 are operatively connected to an information processing unit (not shown in the drawings) having programmed therein operating algorithms for switching the valves and actuating the pumps and vacuum sources. The information processing unit can be connected to electrical, hydraulic, or mechanical manipulators such as servos, robotic arms, gears and the like to operate the pumps, valves, and vacuum source as well as other components of apparatus 10. For example, in one embodiment, hose 22 can be attached to a robotic arm that can move hose 22 between sample container 16 and a different site, for example where another container is located, according to instructions provided by the information processing unit.

Figure 2:
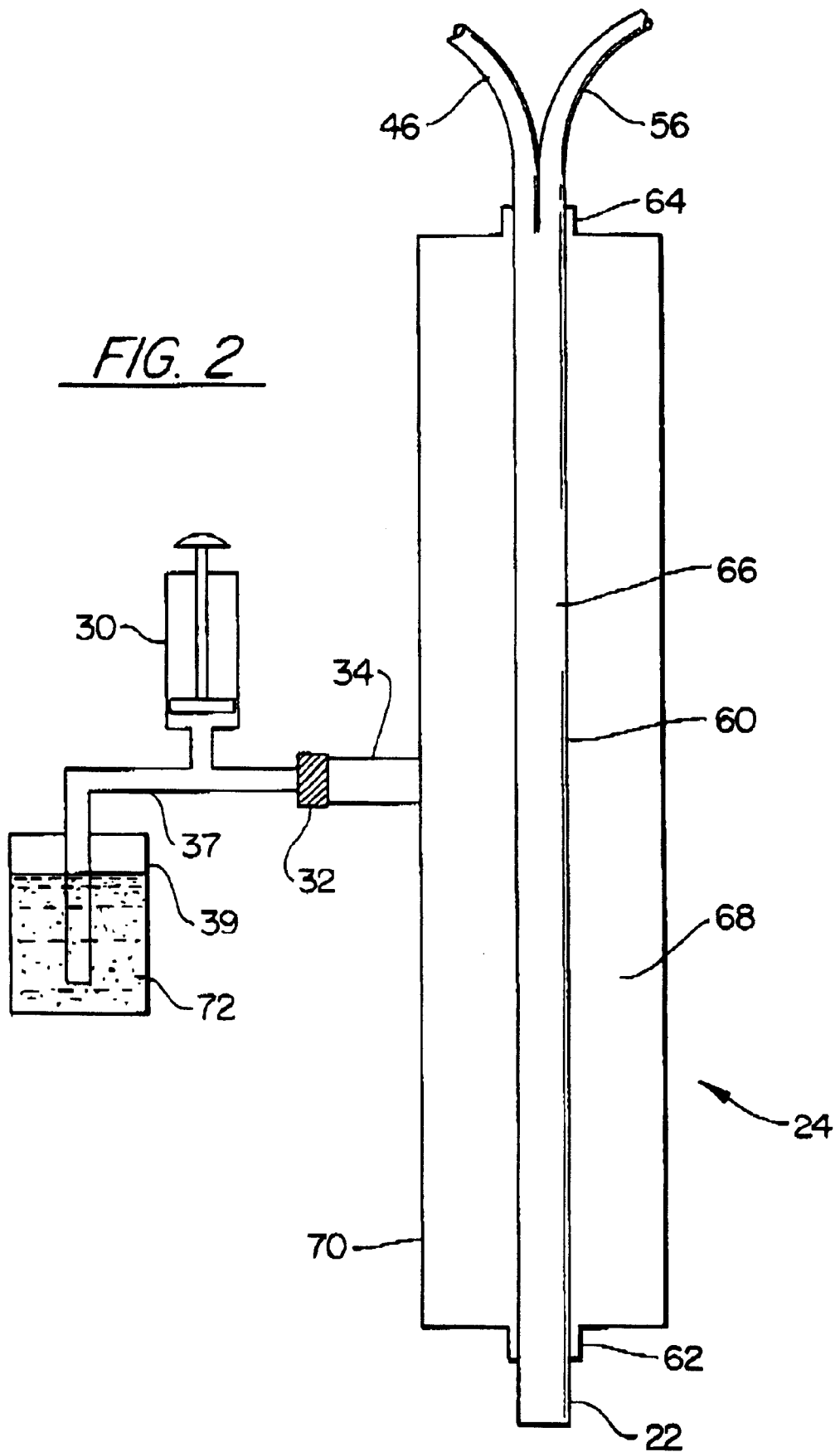
FIG. 2 is a schematic view of a filtration device within the invention.

Referring now to FIG. 2, a particularly preferred embodiment of filtration device 24 is shown in further detail. In this preferred embodiment of the apparatus of the invention, filtration device 24 includes a hollow fiber membrane 60 fashioned into a tube having a wall that defines a lumen 66. The filtration device 24 further includes a bottom port 62, which is longitudinal to the filtration device, so that tubular shaped membrane 60 fluidly connects sample hose 22 and lumen 66. Fluids, such as sample of cells 20, can enter lumen 66 from sample hose 22 by port 62. Filtration device 24 also includes a top port 64, which is longitudinal to the filtration device, so that tubular shaped membrane 60 fluidly connects hoses 46 and 56 to lumen 66. Buffer 49 (not shown) can enter lumen 66 from buffer hose 46 by port 64. Likewise, detergent solution 59 (not shown) can enter lumen 66 from detergent solution hose 56 by port 64.

Although the devices in FIGS. 2, 3 and 4A–K show only one membrane 60. In another preferred embodiment, device 24 can include more than 1 membrane 60 which forms more than 1 lumen 66. More specifically, the filtration device can have 2 membranes each forming a lumen so that the filtration device contains 2 lumens. More preferably, the filtration device contains three membranes which form 3 lumens. Most preferably, the filtration device contains four membranes which form 4 lumens. It has been found having more than 1 lumen will increase the processing flow rate. In addition, having more than 1 lumen will have less fouling and require less cleaning cycles. However, it is also preferred that the filtration device contains less than 20 membranes which form less than 20 lumens, and most preferred that it contains less than 10 membranes which form less than 10 lumens.

As noted in FIG. 2, the outer surface of filtration device 24 preferably includes a non-reactive impermeable housing 70 which envelopes hollow fiber membrane 60 and extramembrane chamber 68. The extramembrane chamber 68 is defined as the space between the inner wall of housing 70 and the outer wall of tubular membrane 60. Vacuum and waste port 34, which can be lateral to the filtration device 24, is an opening that fluidly connects extramembrane chamber 68 to vacuum source 30 and waste hose 37. Port 34 can thus project through the wall of impermeable housing 70, such that application of a vacuum force to port 34, for example from source 30, transfers the vacuum force to extramembrane chamber 68. Vacuum in chamber 68 causes fluid and interferants 72 to be withdrawn from lumen 66 across membrane 60 into chamber 68 and out through port 34. After closing valves 32 and applying a forward hydraulic force from source 30, the withdrawn fluid and interferants 72 can be transported to waste reservoir 39.

Device 24 is preferably arranged such that fluid and interferants can be withdrawn throughout the entire portion of membrane 60 contained within housing 70. For example, port 34 is preferably positioned on the device such that a vacuum from vacuum source 30 is directed approximately perpendicular with respect to the length of membrane 60. Application of a vacuum in such a crosswise manner is preferred as compression of cells is reduced compared to devices that force cells to one end of membrane 60, which occurs when a pump is used to increase pressure within the lumen of membrane 60 to expel cells through the pores of the membrane.

Figure 3:
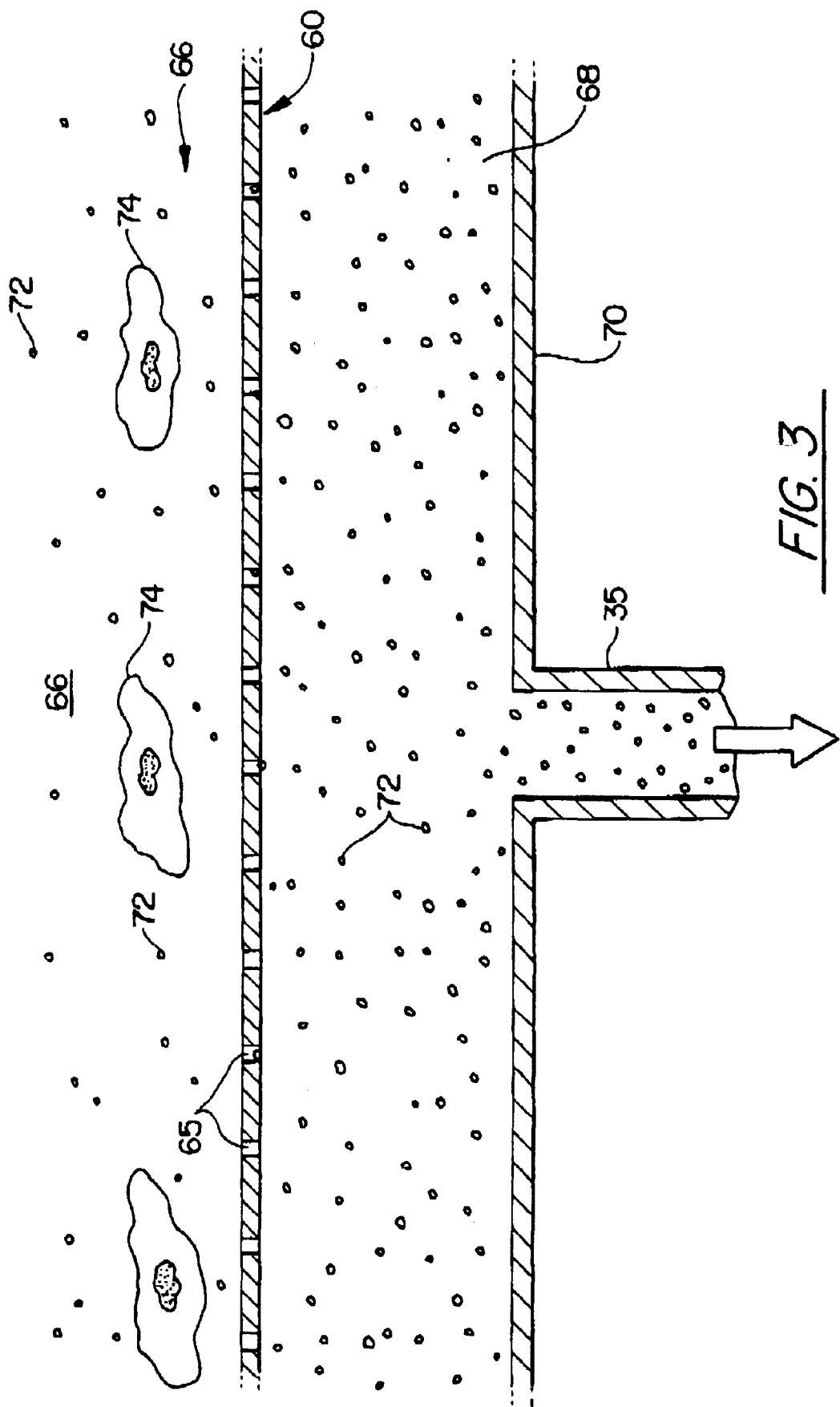
FIG. 3 is a cross-sectional view of the filtration device of the invention shown with interferants removed from a sample of cells within a lumen of a hollow fiber membrane of a filtration device.

A preferred mechanism by which filtration device 24 selectively retains the cells of interest while allowing the interferants to pass through is illustrated in FIG. 3. Sample of cells 20 is shown in lumen 66 as a mixture comprising cells 74 and interferants 72, such as unbound probe and cellular debris, which is dispersed in a liquid medium. Hollow fiber membrane 60 is shown as having a plurality of pores 65 having a mean diameter of less than the mean diameter of cells 74 but greater than the diameter of interferants 72. Interferants 72 can thus pass through pores 65 while the larger diameter cells 74 cannot. Application of a vacuum to chamber 68, through port 34, causes the liquid in which sample of cells 20 is dispersed to be withdrawn through pores 65 into chamber 68 along with interferants 72 contained within the liquid. Cells 74, being too large to pass through pores 65, are selectively retained in lumen 66.

In the embodiment shown in FIG. 3, membrane 60 can be composed of any suitable material. For example, it can be composed of a hydrophobic or hydrophilic polymer. In one preferred version it is composed of microporous polysulfone. Suitable sizes of pores 65 of membrane 60 can be selected by one of skill in the art depending on the particular characteristics of the cell sample to be analyzed. For applications where human leukocytes are analyzed, pores 65 preferably have a mean diameter of between about 0.2 and 2.0 microns, and more preferably have a mean diameter of about 0.3 microns to about 1 micron. The surface area of the membrane 60 can also be selected by one of skill in the art depending on such factors as the particular characteristics of the sample to be analyzed, the sample volume, and the type of membrane used. For example, for a 100 microliter sample of a whole human blood processed and then diluted to a total volume of about 4 ml using an isotonic buffer, 20 cm$^2$ of a hollow fiber membrane with 0.65 micron diameter pores is sufficient to remove the majority of interferants in the sample. For a 1 ml sample, preferred lumen volumes range from about 50 $\mu$l to about 2500 $\mu$l and preferably about 200 $\mu$l to about 1000 $\mu$l, and preferred extramembrane chamber volumes range from about 100 $\mu$l to about 2500 $\mu$l and preferably about 500 $\mu$l to about 1000 $\mu$l. Other lumen and extramembrane chamber volumes can be preferred depending on the volume and types of sample. Membrane 60 can also be treated with non-lytic surfactants such as Pluronic F68 and Pluronic 25R8 (BASF Corp.) to enhance its reusability without having a material adverse effect on cell count or cell marker density on cells in sample 20.

Figure 4A:
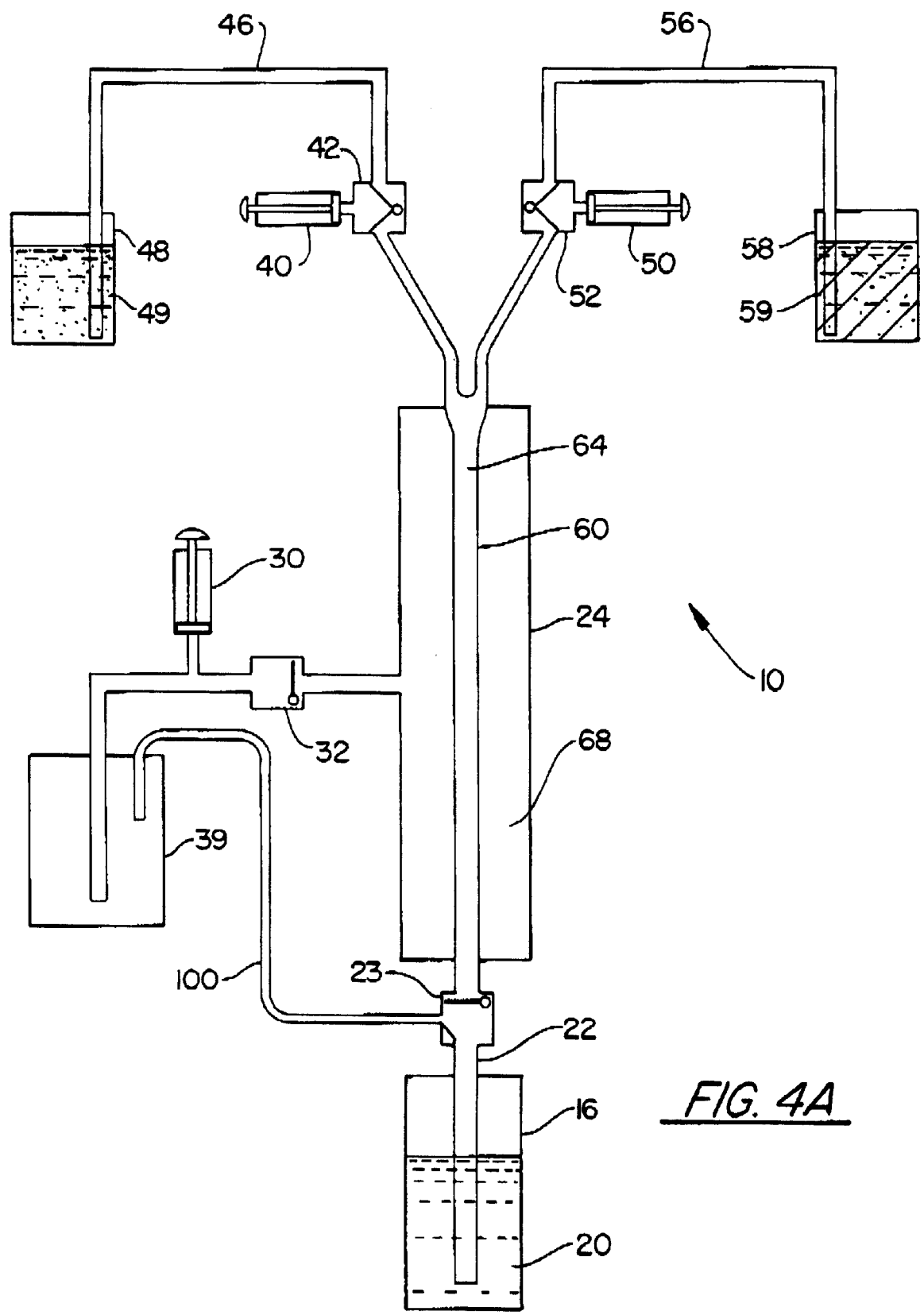
Figure 4B:
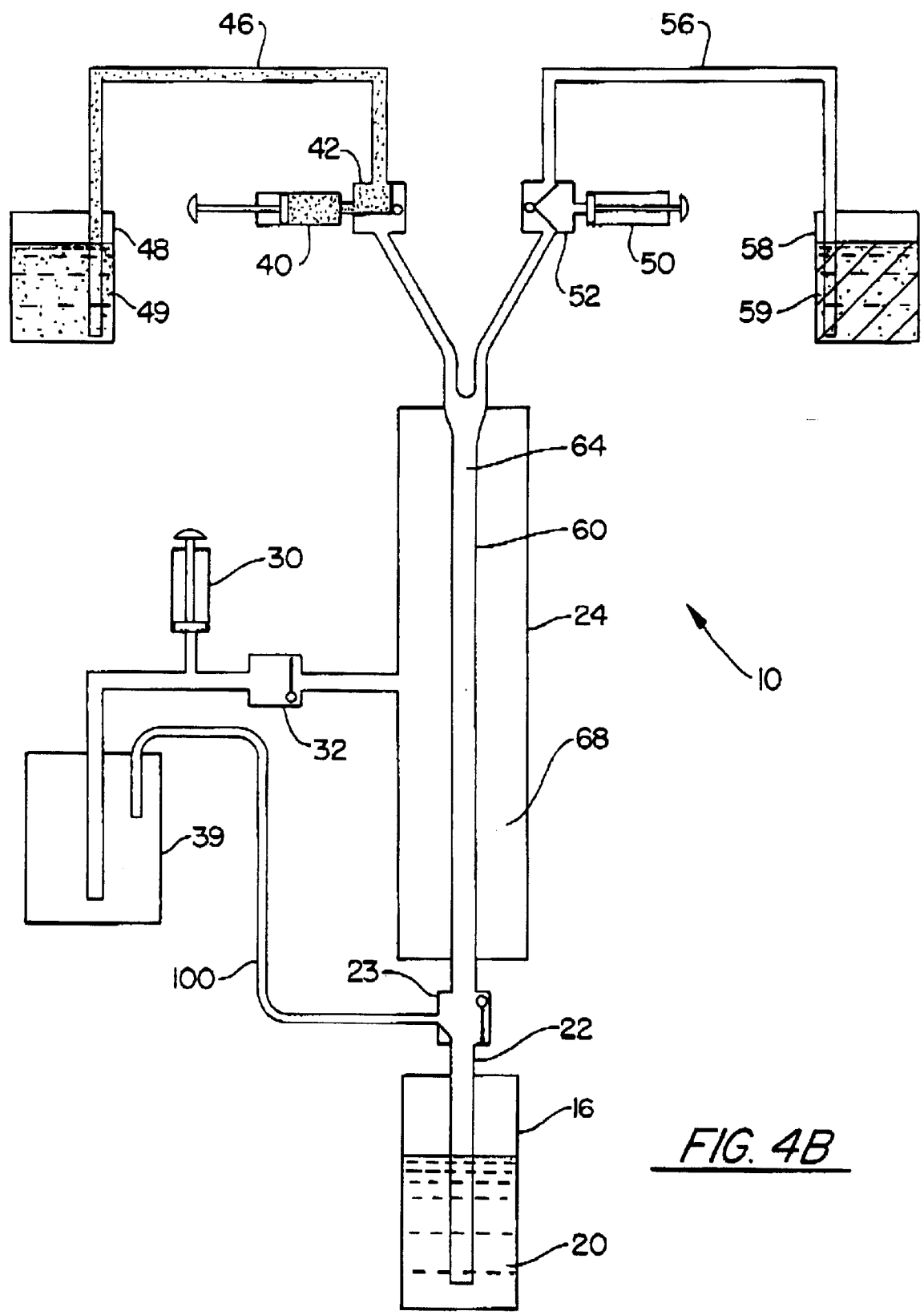
Figure 4C:
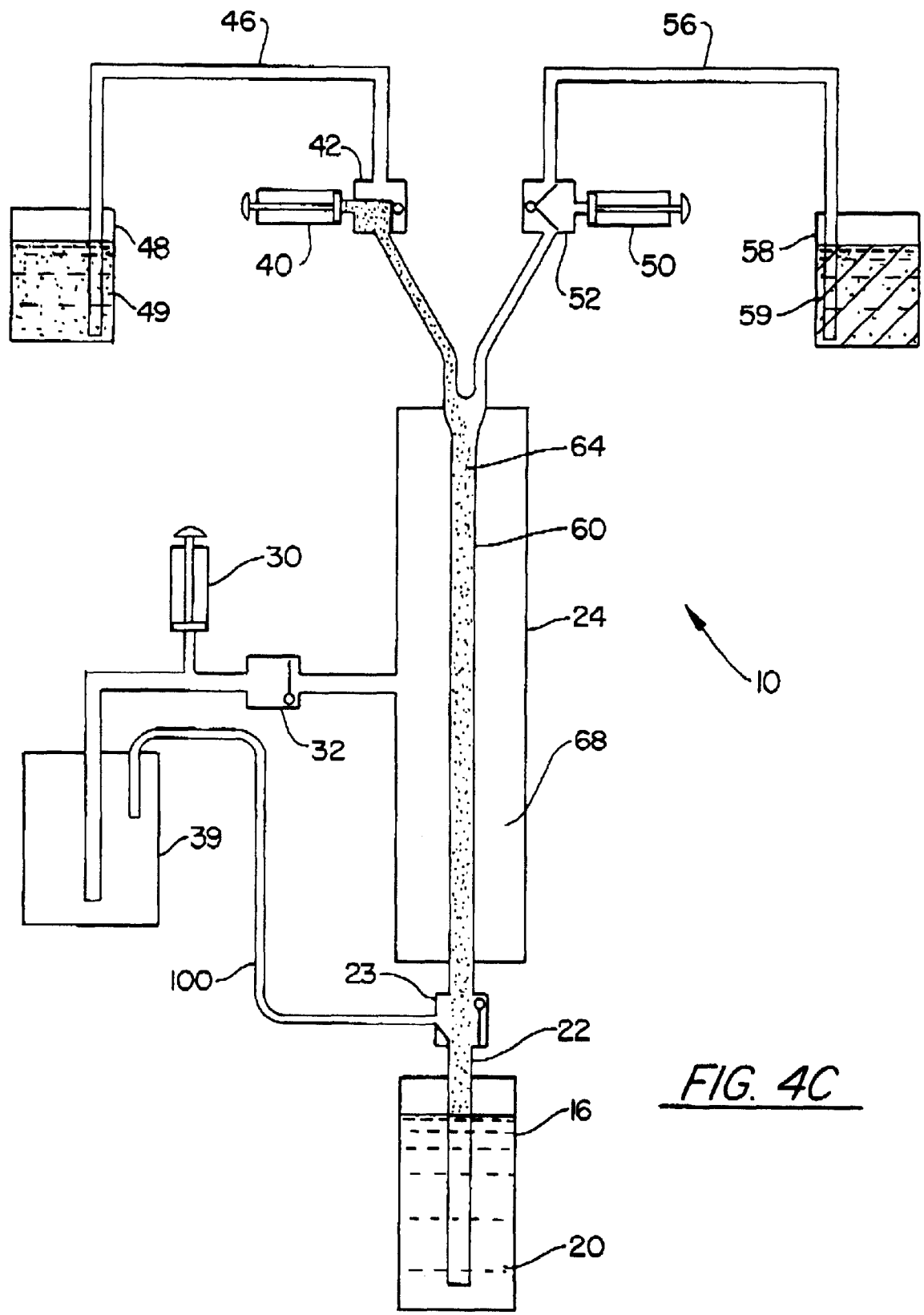

An overview of a preferred operation of an apparatus of the invention is shown in FIGS. 4A–4E. In FIG. 4A, apparatus 10 is shown with sample hose 22 in fluid communication with sample of cells 20. For example, the sample of cells 20 can be 100 $\mu$l of whole blood having been processed using a lysing reagent, a stabilizing buffer, and a fixative such as IMMUNOPREP™ reagents (manufactured by Beckman Coulter, Inc., Miami, Fla.). As illustrated in FIGS. 4B and C, sample 20 is diluted with buffer 49 to facilitate removing a greater percentage of interferants 72. To transfer a predetermined volume of buffer 49, such as to bring the total volume of the sample to about 4 ml, from buffer reservoir 48 into sample container 16, apparatus 10 is arranged by a computer control mechanism (not shown), so that valve 23 is open, and valves 32 and 52 are closed. As shown in FIG. 4B, buffer valve 42 is then switched to the fill position and buffer pump 40 is activated to aspirate the predetermined volume of buffer 49. As indicated in FIG. 4C, valve 42 is then switched to the dispense position and pump 40 is activated to dispense the aspirated volume of buffer 49 through filtration device 24 into sample container 16 thereby diluting sample of cells 20.

Figure 4D:
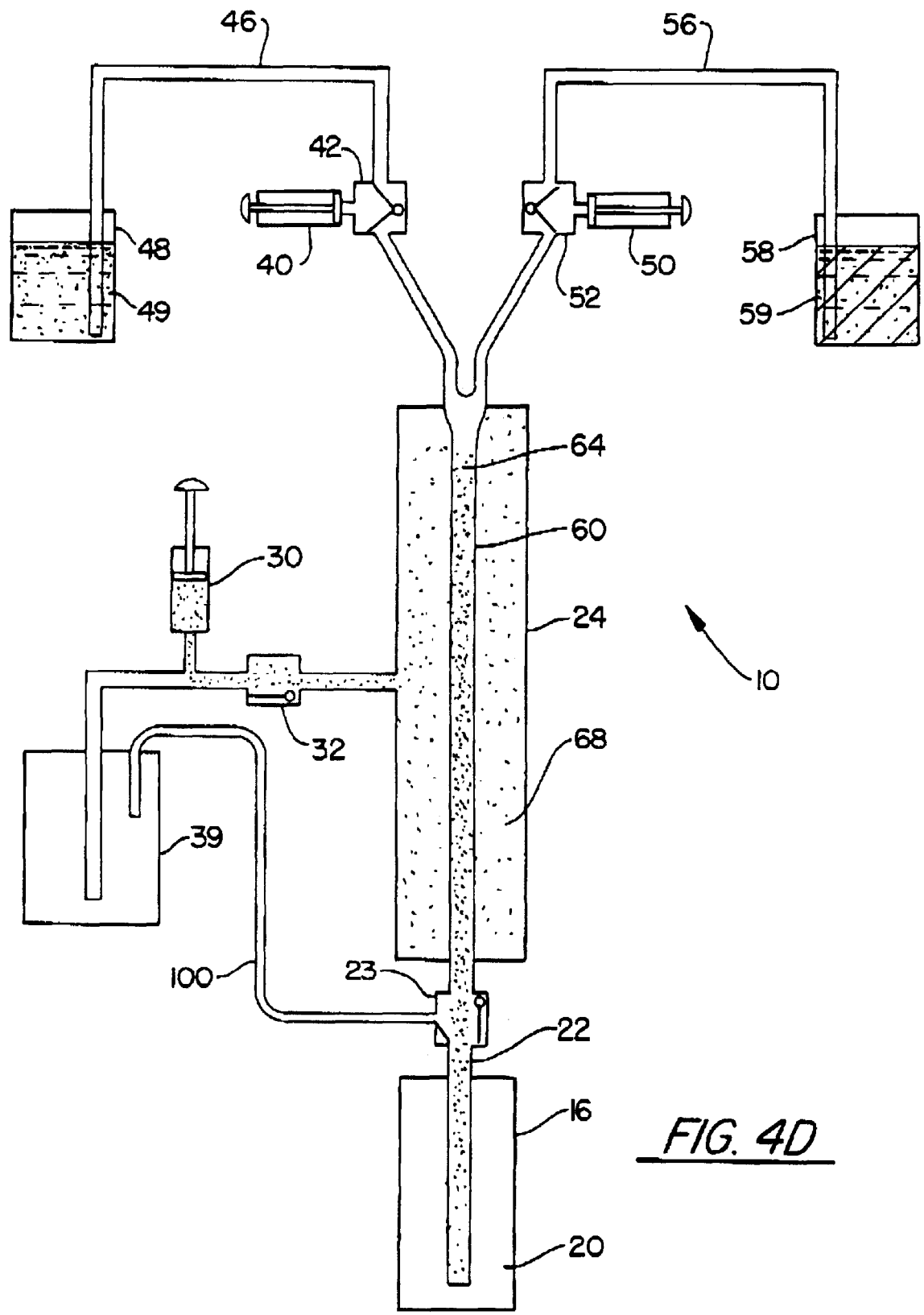
Figure 4E:
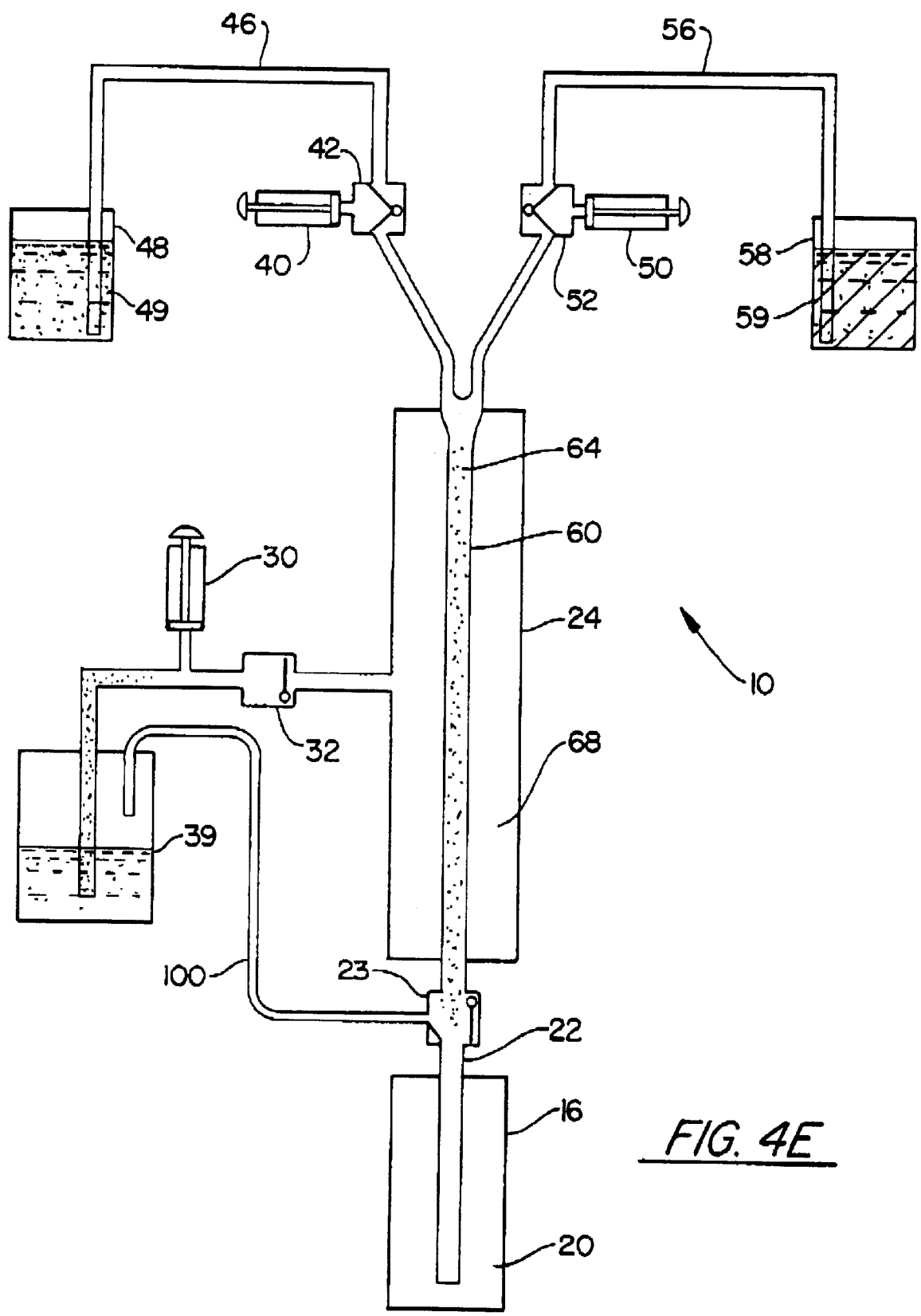

As shown in FIG. 4D, sample 20 is then aspirated into filtration device 24 where interferants are removed from the sample by having them pass through membrane 60. In this step, apparatus 10 is configured so that valves 42 and 52 are closed, and valves 23 and 32 are open. Vacuum source 30 is then activated to produce a vacuum to aspirate sample of cells 20 from container 16 into filtration device 24. While the vacuum is being supplied, the liquid in sample 20 that contains interferants is passed through device 24 into vacuum source 30, while cells are retained in device 24, within lumen 66. As shown in FIG. 4E, valves 32 are then closed and vacuum source 30 is activated to provide a forward hydraulic force to expel the aspirated liquid through waste hose into waste reservoir 39.

Figure 4F:
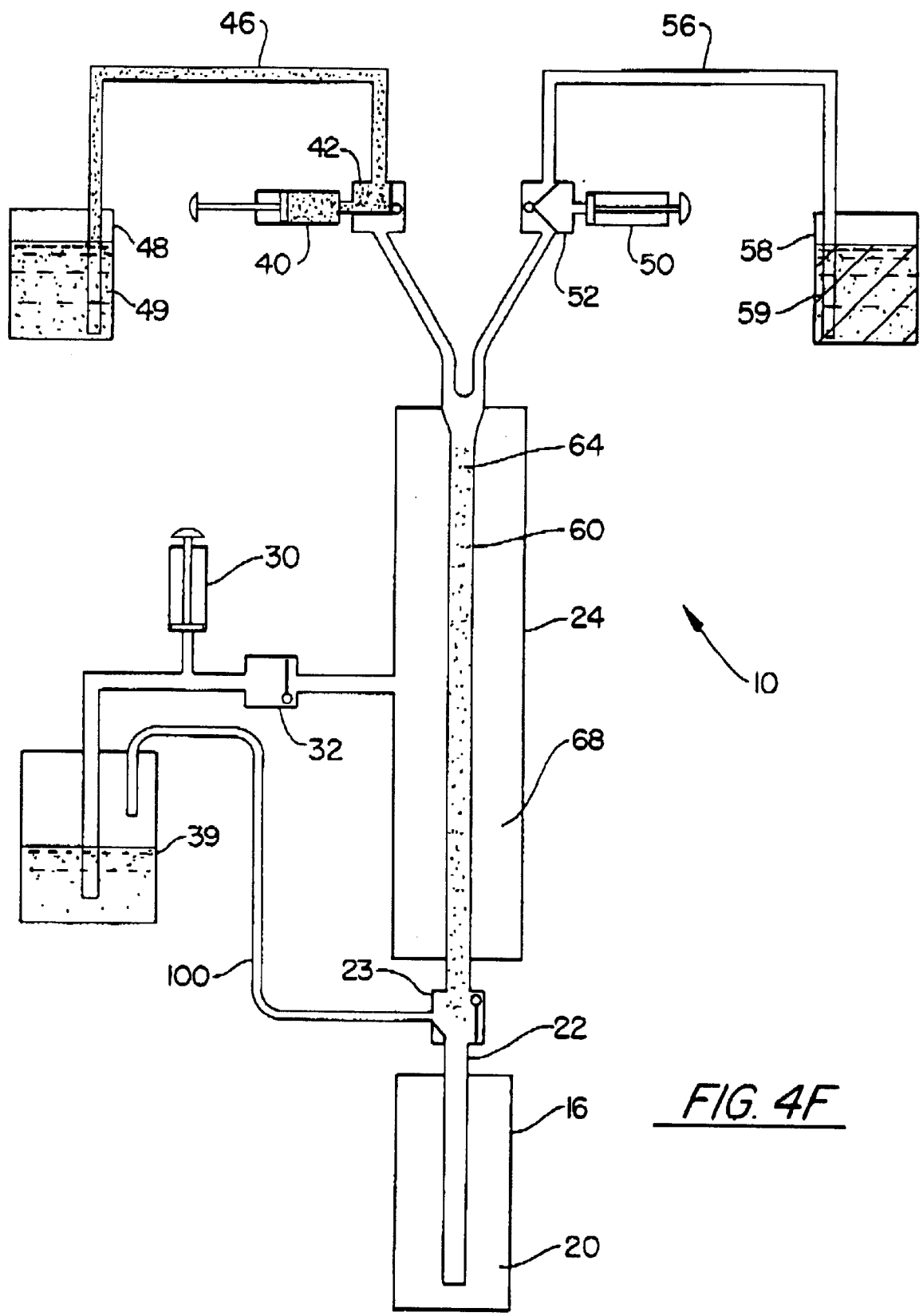
Figure 4G:
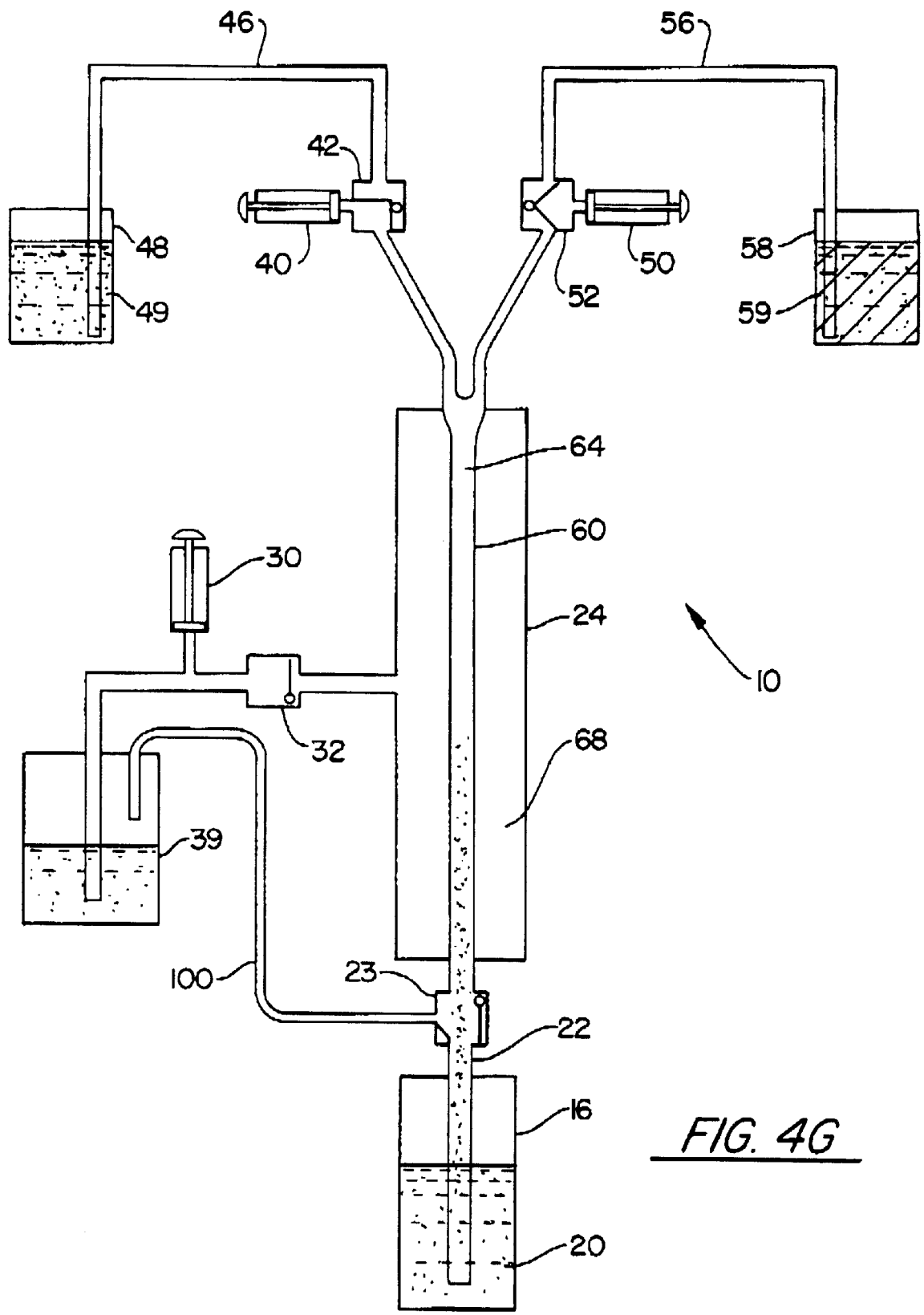

As illustrated in FIGS. 4F and G, sample of cells 20 from which interferants have been removed is then transferred back into container 16. In this step, apparatus 10 is configured so that valve 23 is open, and valves 32 and 52 are closed. In FIG. 4F, buffer valve 42 is then switched to the fill position and buffer pump 40 is activated to aspirate a predetermined volume of buffer 49, for example 1.25 ml, from buffer reservoir 48. Valve 42 is then switched to the dispense position and pump 40 is activated to dispense the aspirated volume of buffer 49 through filtration device 24 into sample container 16 as illustrated in FIG. 4G. Movement of buffer 49 through device 24 flushes sample of cells 20 from the device into container 16. In an alternative embodiment (not shown), an additional fluid connection from device 24 to a clean sample container rather than sample container 16 can be provided, such that after the interferants have been removed from sample of cells 20, the sample can be transported from device 24 to the clean container.

Figure 4H:
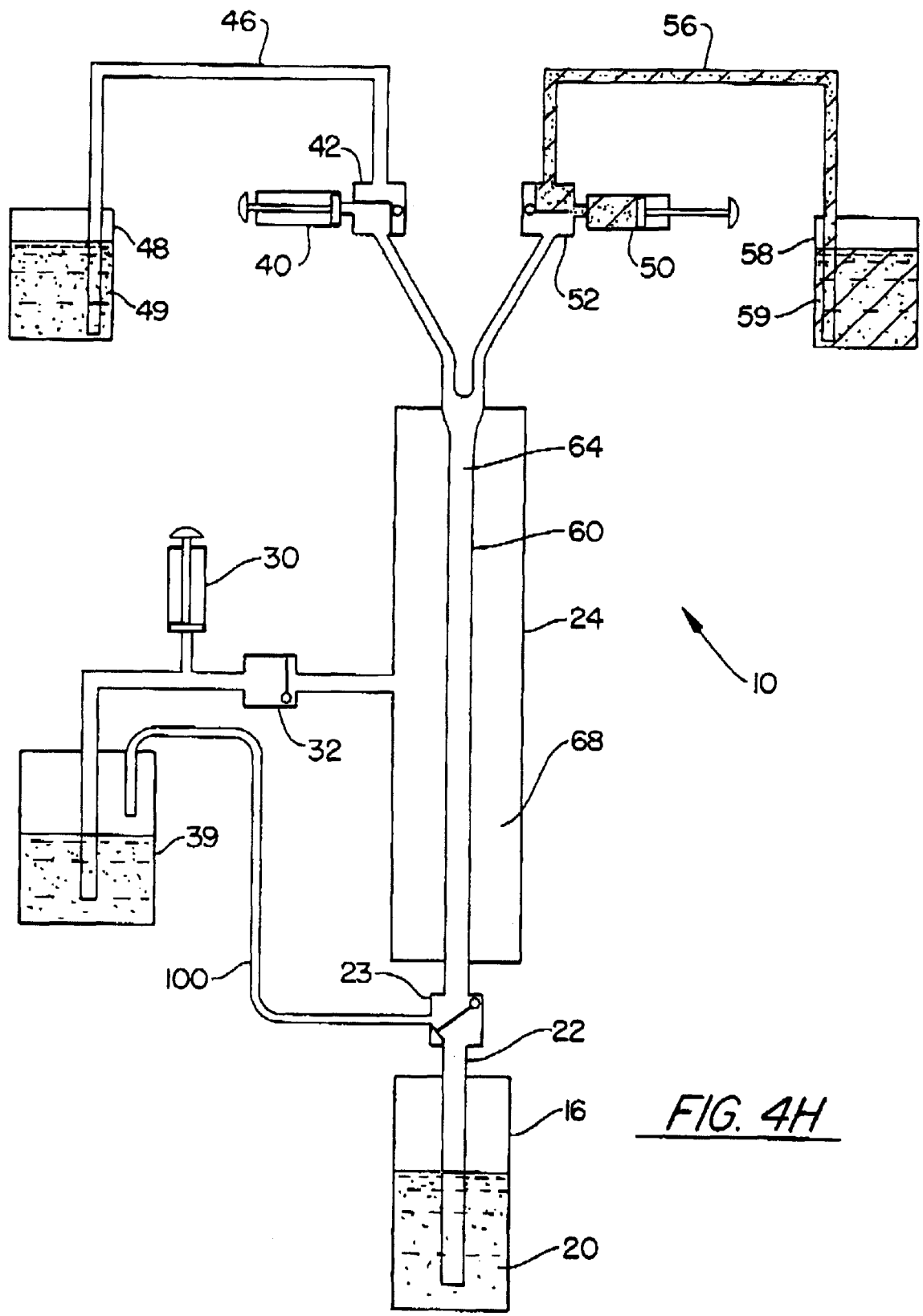
Figure 41:
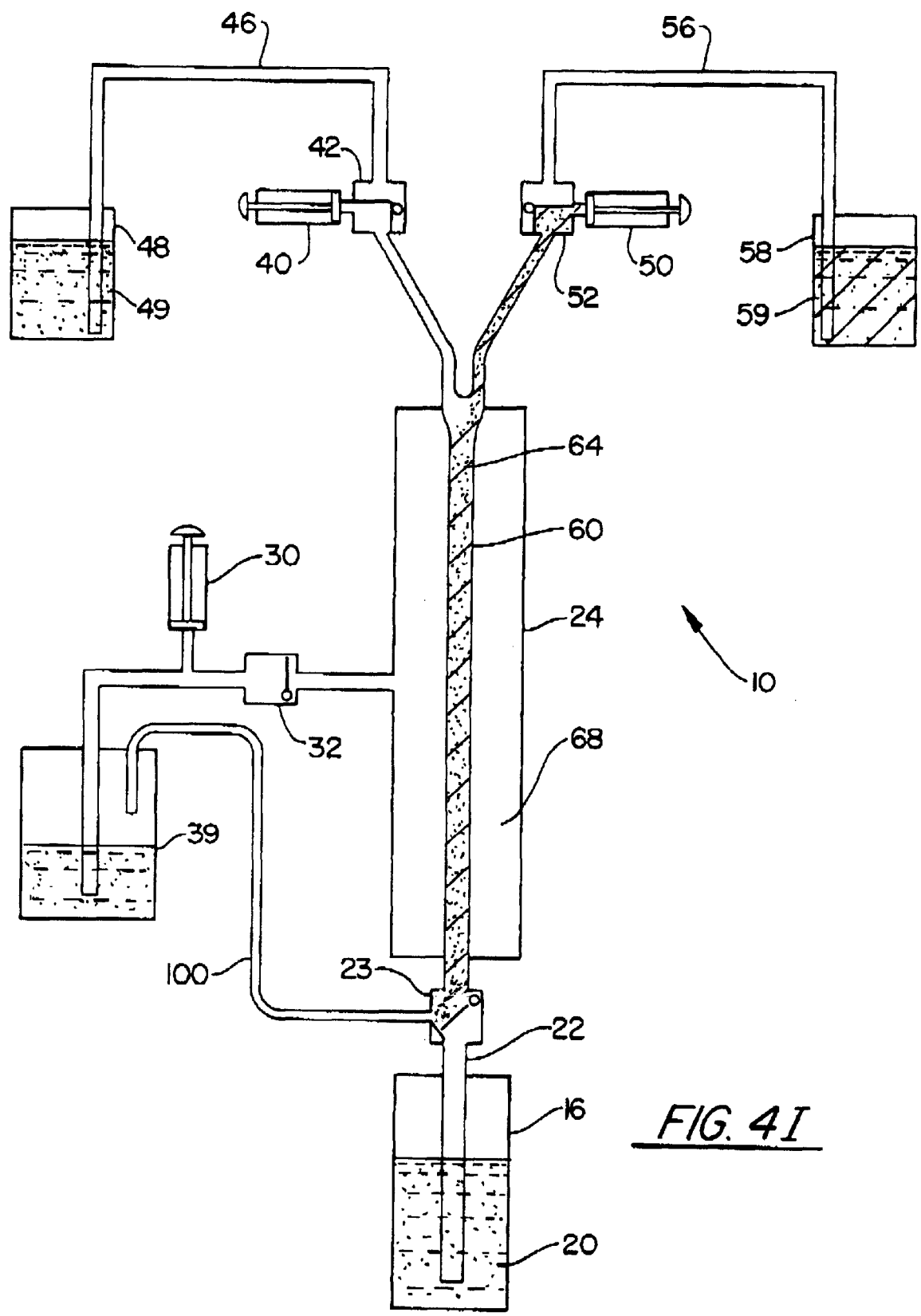
Figure 4J:
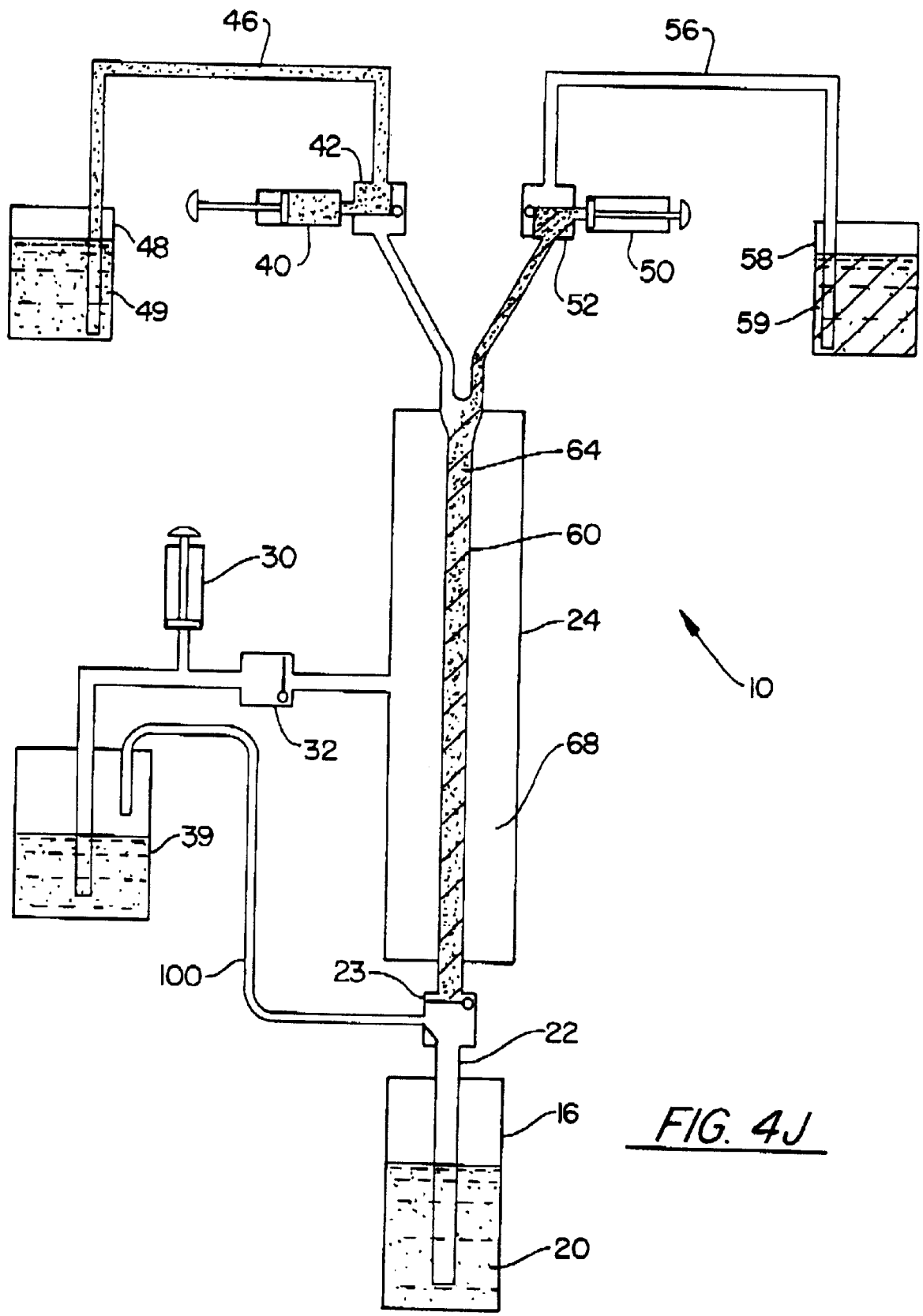

The apparatus 10 can be washed as shown in FIGS. 4H–K. The washing of the apparatus can be after each sample, after a predetermined number of samples, or upon fouling of the membrane 60. In the washing step, apparatus 10 is set up so that valve 23 is partially open, and valves 32 and 42 are closed. As shown in FIG. 4H, detergent solution valve 52 is then switched to the fill position and detergent solution pump 50 is activated to aspirate a predetermined volume of detergent solution 59, for example 3 ml, from detergent solution reservoir 58. As indicated in FIG. 4I, valve 52 is then switched to the dispense position and pump 50 is activated to dispense the aspirated volume of solution 59 through filtration device 24. Because valve 23 is partially open, solution 59 can flow through hose 100 into waste reservoir 39. To purge any detergent solution 59 remaining in device 24, as shown in FIG. 4J, buffer valve 42 is then switched to the fill position and buffer pump 40 is activated to aspirate a predetermined volume of buffer 49, for example 3 ml, from buffer reservoir 48.

Figure 4K:
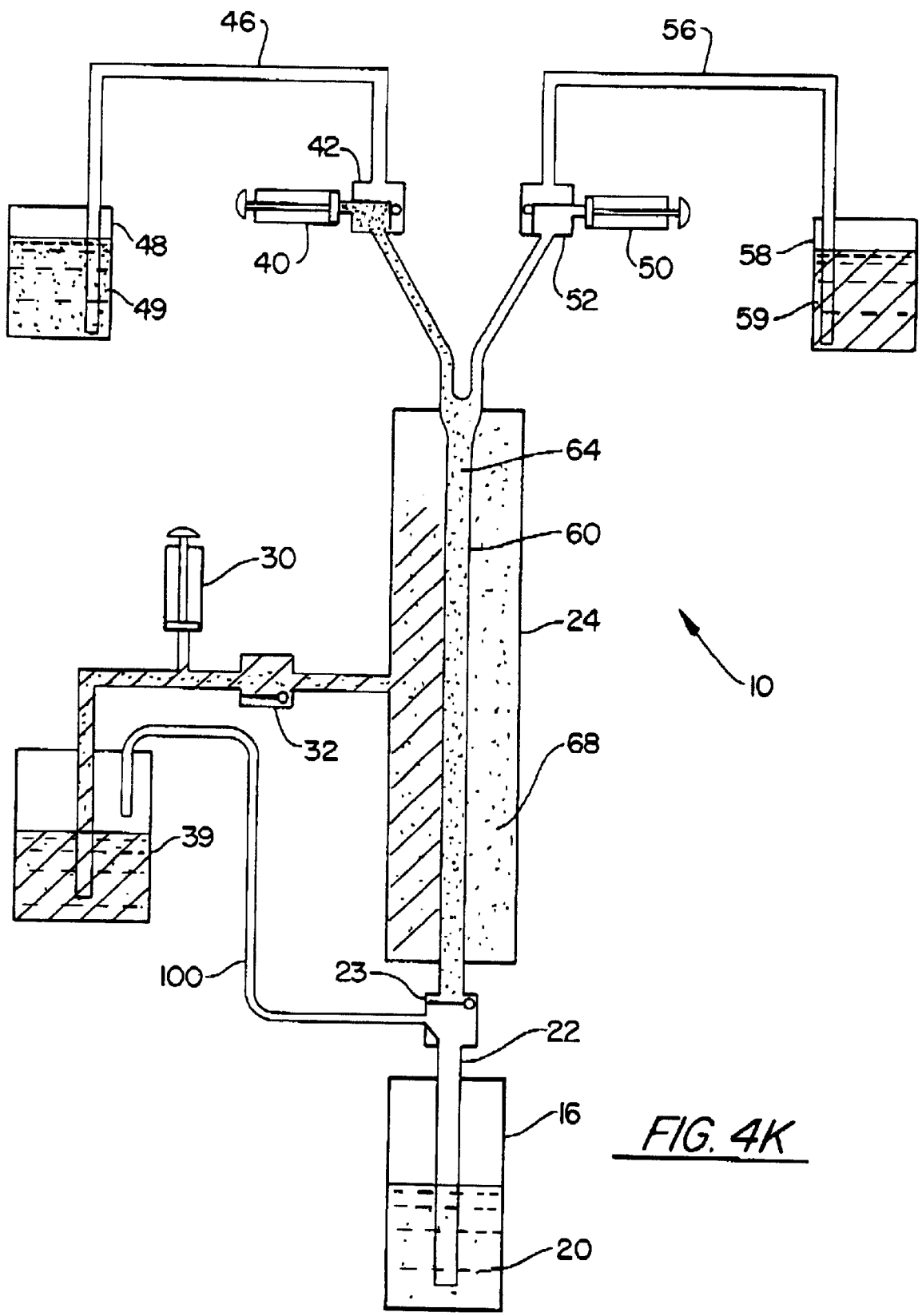

In FIG. 4K, prior to the buffer dispensing step, valve 23 can be closed and valve 32 can be switched to the open position. Valve 42 is switched to the dispense position and pump 40 is activated so that buffer 49 is dispensed and the remaining detergent solution 59 in the filtration device and buffer 49 are transferred to waste reservoir 39 by a waste hose. Alternatively, or in addition, valve 23 is switched to being partially open, and valve 32 is closed, and valve 42 is switched to the dispense position and pump 40 is activated to dispense the aspirated volume of buffer 49 through filtration device 24 and hose 100 into reservoir 39. The foregoing steps can be repeated so that device 24 is washed with multiple volumes of buffer prior to analysis of the next sample.

Referring now to FIG. 5, the invention also includes methods for removing interferants from a sample of cells. A preferred method for removing interferants from a sample of cells comprises a first step 80 of applying a vacuum force to a blood cell sample to cause the blood cell sample to leave the sample container 16 and contact a filter. As previously explained, this is accomplished by a vacuum force, which typically is capable of causing approximately 4 ml of a blood cell sample to be withdrawn from the sample container and pass through the membrane filter in approximately 7 seconds. As appreciated by one skilled in the art, the amount of blood cell sample withdrawn from the sample container 16 can be increased or reduced and the time can also be increase or reduced. The limitation on the vacuum force is that it will be less than the amount of force that would cause the cells to aggregate when being retained in the lumen 66. Preferably, the force will be less than that which would cause the cells to deform.

The method includes a second step 82 of applying a force to the blood cell sample in contact with the filter, whereby interferants in the blood cell sample pass through the filter while the cells of interest in the blood cell sample do not pass through the filter. In a preferred embodiment of the invention, the force that is applied to the blood cell sample to cause the interferants to pass through the filter is the same vacuum force which is used to withdraw the blood cell sample from the sample holder. However, it is appreciated that the force could be a separate hydraulic force which after the blood cell sample is withdrawn from the sample container 16, could be applied to the blood cell sample to push the blood cell sample into the lumen and through the membrane. However, it has been found that a vacuum is less damaging to cells. The limitation on the force is that it will be less than the amount of force, which would cause the cells to aggregate when being retained in the lumen 66. Preferably, the force will be less than that which would cause the cells to deform.

The method includes a third step 84 of recovering the cells from the filter. In a preferred embodiment, the cells are recovered by the apparatus of the invention wherein a volume of buffer is pumped through the top portion of the lumen causing the cells that were retained in the lumen to pass through the bottom portion of the lumen back into the sample container. Alternative, the retained blood cells can pass through the bottom portion of the lumen into a new sample container which can be employed to store the recovered blood cells.

In a more preferred embodiment of the present method, the blood cell sample is first diluted with at least one volume of buffer to each volume of blood cell sample. Even more preferable is that the blood cell sample be diluted with at least two volumes of buffer before entering the lumen to remove the interferants. It has been found that with a one volume dilution of the blood cell sample that greater than 70% of the interferants are removed from the blood cell sample, and with a two volume dilution, greater than 80% of the interferants are removed from the blood cell sample. A three volume dilution of the blood cell sample is preferred to remove greater than 90% of the interferants from the blood cell sample.

The steps of this method can be accomplished using the apparatus of the invention which will provide automation of the steps described above. As defined herein, one cycle of the method is considered to be one wash cycle of the blood cell sample. More specifically, one wash cycle of the blood cell sample comprises applying a vacuum force to a blood cell sample to cause the blood cell sample contact a filter; applying a force to the blood cell sample in contact with the filter, whereby interferants in the blood cell sample pass through the filter while the cells in the blood cell sample do not pass through the filter; and recovering the cells from the lumen. Accordingly, one wash cycle of the blood cell sample wash cycle of this invention can be performed in less than 5 minutes. Preferably, one wash cycle of the blood cell sample is performed in less than 3 minutes, and more preferably less than 1 minute. In an even more preferred embodiment one wash cycle of the blood cell sample is performed in less than 30 seconds. Finally, in a most preferred embodiment, one wash cycle of the blood cell sample is performed in less than 15 seconds.

It has been found that multiple wash cycles cause the cells to deteriorate such as shrinkage of the cell membranes and rupture of the cell membranes. It has been further found that the addition of a serum substance to the buffer which dilutes the blood cell sample minimizes the deterioration. As defined herein, serum substance comprises cholesterol, cholesterol esters, and cholesterol which has been combined with one or more other compounds found in serum plasma, and mixtures thereof. Preferably, such other compounds further comprise lipoproteins and phospholipids, and mixtures thereof. As appreciated by those skilled in the art, typically cholesterol will contain approximately 30% esters. As further appreciated by those skilled in the art, the lipoprotein will maintain the cholesterol in an aqueous solution. Preferably, the serum substance is selected from the group comprising cholesterol, cholesterol esters, lipoprotein cholesterol, lipoprotein cholesterol esters, cholesterol combined with phospholipids and mixtures thereof.

Figure 14:
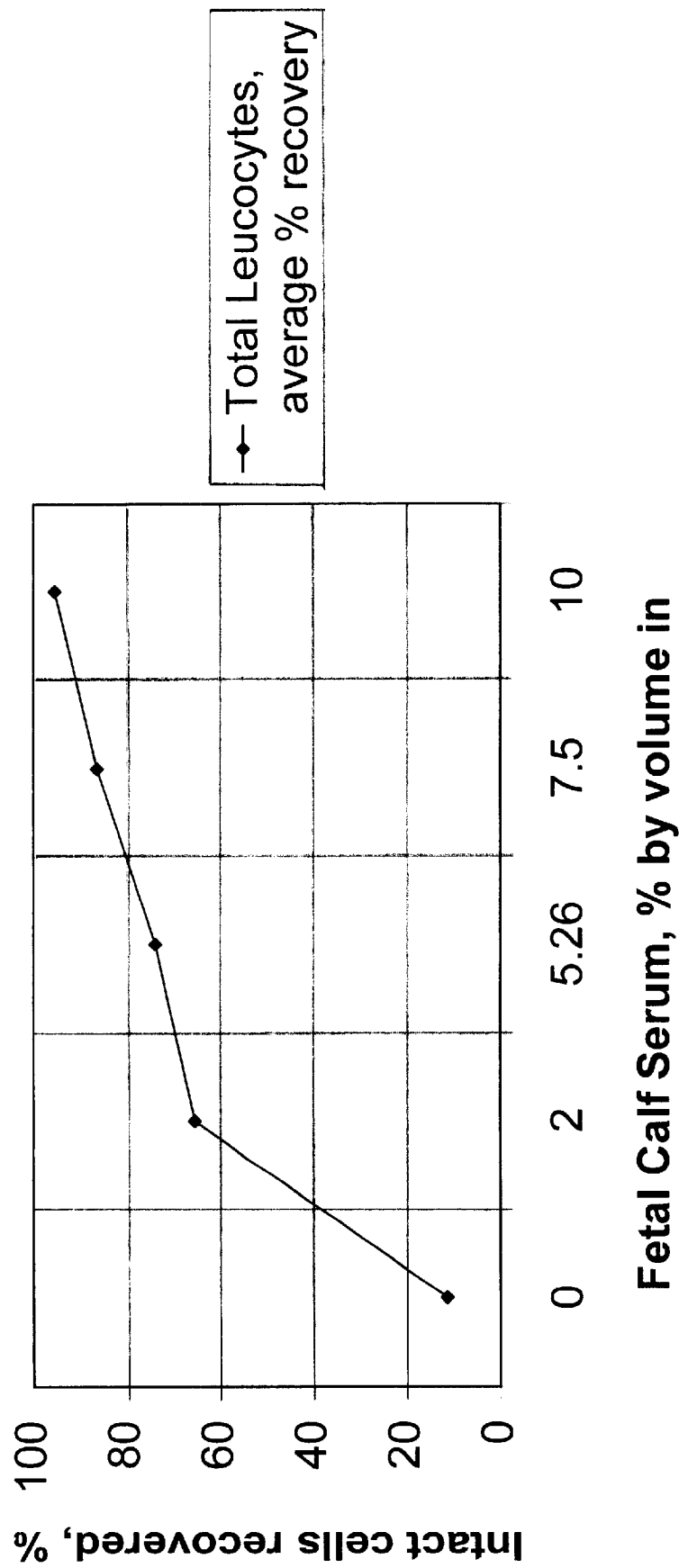
FIG. 14 is a graph showing the percent of intact cells recovered after three wash cycles wherein the wash buffer had increasing amounts of fetal calf serum.

FIG. 14 depicts an increase in the recovery of cellular events as related to the percent addition of fetal calf serum in a buffer. In this figure, the blood cell sample was washed 3 times with a hollow fiber membrane apparatus shown as "Invention" in the figure. An increase of fetal calf serum indicates that there will be an increase in the percent of cells recovered after multiple wash cycles.

It has also been found that one wash cycle of the blood cell sample without the addition of a serum substance eliminates the banana appearance between the lymphocytes and neutrophils subpopulations in histograms of blood cell samples containing a high lipid content.

In an example of the present method, first step 80 is performed by providing a sample of cells such as a 100 microliters of whole human blood obtained by venipuncture from a human subject. If the removal of erythrocytes is desired, the sample can be diluted in a reagent which lyses red blood cells such as 600 microliters of formic acid, and then further diluted by addition of a reagent that neutralizes the red blood cell lysing agent such as 265 microliters of a carbonate buffer. Optionally, a fixative such as 100 μl of a paraformaldehyde solution can also be added to fix the cell sample. The blood cell sample is diluted to a total volume of about 4 ml with an isotonic buffer. Suitable reagents for these steps can be obtained from Beckman Coulter, Inc. (IMMUNOPREP™ reagent system part no. 7546999 or SCATTER PAK™ reagent system). A vacuum force is then applied to the diluted blood cell sample to cause it to contact a filter. Preferably the filter is a hollow fiber membrane (e.g., Cat #CFP-6-D-H22LA from A/G Technology Corporation).

In second step 82, a force is applied to the blood cells sample which is in contact with the filter to cause the interferants in the diluted blood cell sample to pass through the filter while the cells of interest in the blood cells sample are retained by the filter. More specifically, the cells of interest in the diluted blood cell sample do not pass through the filter. When the hollow fiber membrane is used, the cells of interest will be retained in the lumen. Preferably, a vacuum force is applied to the blood cell sample to cause the interferants to pass through the lumen while the cells of interest are retained in the lumen.

In a most preferred embodiment, the vacuum force that is used to cause the interferants to pass through the filter also aspirates the blood cell sample from the sample container. More specifically, the filtration device is in fluid communication with the sample container since it is filled with a buffer. Therefore, when a sufficient vacuum force is applied to the diluted blood cell sample in the sample container, the diluted blood cell sample is aspirated from the sample container into the filtration device and the interferants pass through the filter. This is accomplished by a continuous flow of the blood cell sample from the sample container through the filter. As previously discussed, the apparatus of this invention can automatically apply the vacuum force necessary to perform these functions.

The Third step 84 is recovering the cells from the filter. This can be accomplished by providing a force, such as a flow of liquid, to the filter in a direction opposite the direction from which the blood cell sample contacted the filter in step 80. The flow of liquid will move the cells of interest away from the filter. The recovered cells can thereafter be transported by fluid communication to an analytical instrument. Preferably, the recovered cells are returned to a test tube that is then transported to an instrument for analysis.

Referring now to FIG. 6, methods for analyzing cells for phenotypic markers are also included in the invention. A preferred method of analyzing a phenotypic marker on cells within a sample includes: a first step 90 of adding a probe that binds the phenotypic market to the sample of cells to be analyzed to form a test sample mixture; a second step 92 of applying a vacuum force to a blood cell sample to cause the blood cell sample contact a filter; a third step 94 of applying a force to the blood cell sample in contact with the filter, whereby interferants in the blood cell sample pass through the filter while the cells in the blood cell sample do not pass through the filter; a fourth step 96 of recovering the cells from the filter. The method can further include a fifth step 98 (not shown) of quantifying the amount of probe and differentiating the cell populations.

Steps 92, 94 and 96 can be performed as described above for FIG. 5 for Steps 80, 82 and 84 respectively. Step 98 can be performed by analyzing the test sample from which the interferants have been removed using flow cytometry or a similar analytical device.

For example, in a preferred version of this method, first step 90, a saturating concentration of a fluorescently-labeled antigen-specific antibody is added to the blood cell sample to form the test sample mixture. And fifth step 98 can be performed by running the processed test sample mixture on a flow cytometer equipped to quantitatively measure the amount of fluorescently-labeled antigen-specific antibody associated with each cell in the processed test sample mixture.

From the foregoing, it can be appreciated that the apparatus and methods of the invention facilitate the removal of interferants from a sample of cells to be analyzed. The invention will be further described in the following examples, which do not limit the scope of the invention described in the claims.

EXAMPLE 1

Cell Washing Apparatus

An apparatus was built with a hollow fiber membrane cartridge cat #CFP-6-D-H22IA from A/G Technology Corporation. The apparatus included a carousel-type cell sample holder adapted to hold several 12×75 mm culture tubes. Alternatively, the apparatus can include other types of tube holders such as a cassette. The apparatus also included various hoses, valves, and pumps so that a sample of cells could be aspirated from the tube, filtered through the hollow fiber membrane cartridge to remove interferants from the sample, and then returned to the tube. As described in the detailed description (for example see, discussion of FIGS. 4A–4K), the apparatus also included various hoses, valves, and pumps so that waste fluids (for example, filtrate containing interferants) could be removed to a waste reservoir, and the hollow fiber membrane could be cleaned for use with additional samples. The apparatus also included a computerized system for coordinating the cell sample washing process and the membrane cleaning procedure. The carousel-type cell sample holder was rotatable and also controlled by the computerized system such that after processing a first cell sample, a second tube containing a second cell sample could be repositioned to allow the second cell sample to be aspirated from the tube, filtered through the hollow fiber membrane cartridge to remove interferants from the sample, and then returned to the second tube. This cycle was repeatable such that all samples in the carousel could be washed.

EXAMPLE 2

Method of Washing Cells

Various methods, including a method employing the apparatus of Example 1, were used for removing interferants from a cell sample processed according to the general method described below. A cell population was stained with a fluorescently labeled antibody according to standard techniques. For example, 100 ul of whole human blood was obtained by venipuncture from a human subject, and then 10 ul of a 1 mg/ml solution of an antigen-specific FITC-labeled antibody was added to the blood sample. Samples were then incubated for 10 minutes at room temperature, after which erythrocytes were lysed using Beckman Coulter's IMMUNOPREP research system and TQ-Prep apparatus according to the manufacturer's instructions (600 $\mu$l of solution A for 8 seconds with mixing; 265 $\mu$l of solution B for 10 seconds with mixing; and 100 $\mu$l of solution C for 10 seconds with mixing). Separate aliquots of the processed blood cells samples were then subjected to one of three different protocols:

A. diluted with an isotonic buffer to a total volume of about 4 ml and then washed 1 time per a "Quick Spin" wash protocol. The Quick Spin was protocol means centrifuge 400×g for 5 minutes using a standard centrifuge, decant supernatant, and resuspend in 1 ml of an isotonic buffer;

B. diluted with an isotonic buffer to a total volume of about 4 ml and then washed 1 time per a "Sorvall" protocol using a Sorvall® Cell Washer 2 (auto mode 80 seconds; high speed 2950–3000 rpm; decant 600 rpm) according to the manufacturer's instructions (washed cells resuspended in final volume of 1 ml isotonic buffer); or C. diluted with an isotonic buffer to a total volume of about 4 ml and then washed 1 time using the apparatus described in Example 1 (washed cells in final volume of 1 ml isotonic buffer).

EXAMPLE 3

Analysis of Cell Samples

Figure 7:
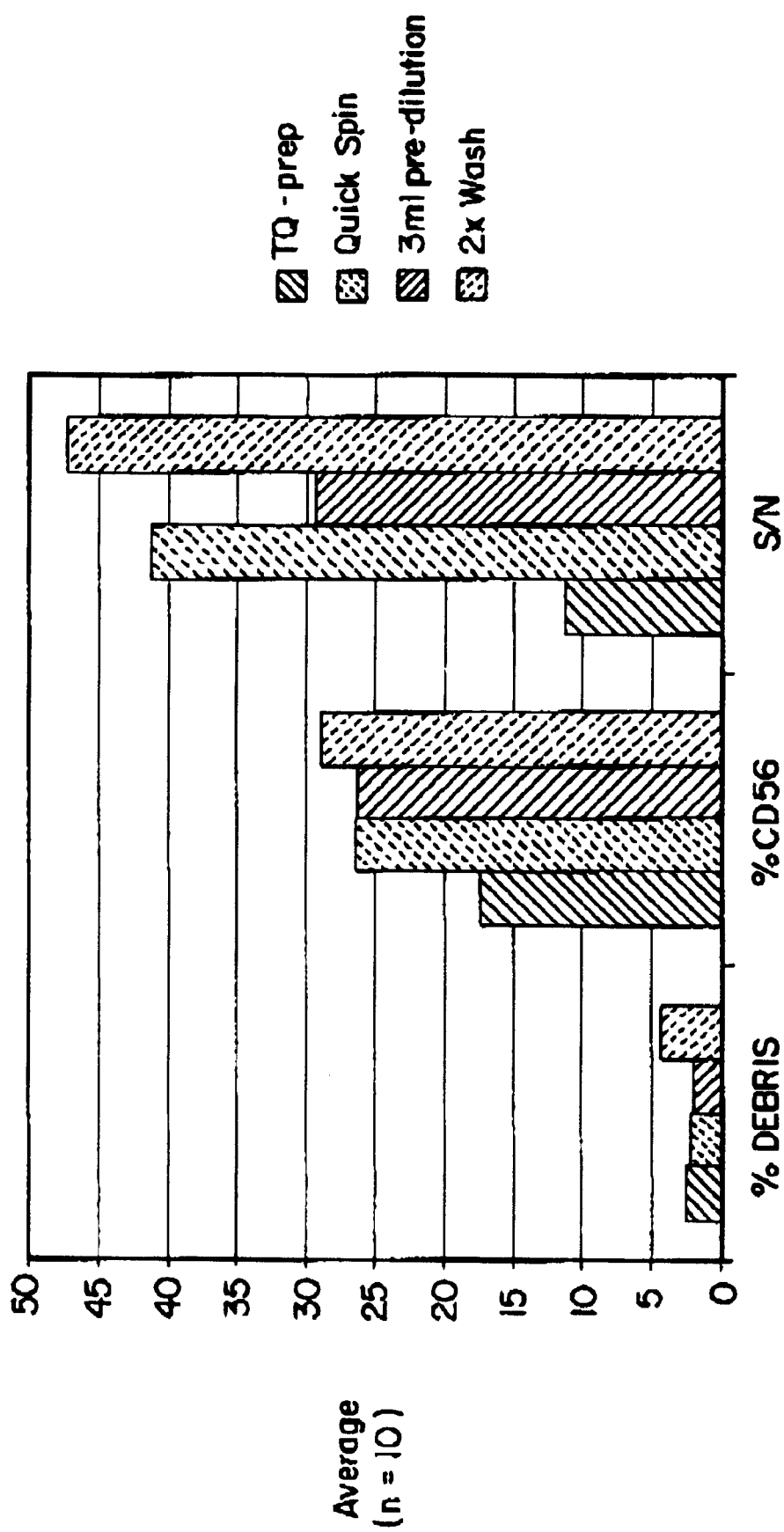
FIG. 7 is a graph showing data obtained from flow cytometric analysis of blood cell samples reacted with fluorescent labeled CD56 monoclonal antibodies. Data are presented as percent debris, percent CD56$^+$, and signal-to-noise ratio. Data shown are averages of ten replicates using one donor.

Samples of whole human blood were reacted with a fluorescent labeled monoclonal antibody directed against the cell surface antigen designated CD56, erythrocyte lysed and fixed according to Example 2. "TQ-Prep" samples were not washed. "Quick Spin" samples were washed according to the Quick Spin protocol described in Example 2. "3 ml predilution" samples were washed one time using a hollow fiber membrane apparatus according to the protocol described in Example 2C. "2× wash" samples were washed two times (second wash with a 2 ml predilution) using a hollow fiber membrane apparatus according to the protocol described in Example 2C. The processed blood cell samples were then subjected to flow cytometric analysis using a COULTER EPICS XL flow cytometer according to the manufacturer's instructions. Results for %debris as determined by light scatter analysis, % CD56 positive cells, and signal-to-noise ratio (extrapolated from histograms) are shown in FIG. 7.

The amount of debris was low for all samples, although more debris was noted in the samples subjected to two washings with the hollow fiber membrane apparatus. The increase of debris was caused by cell degradation because no serum substance was employed in the diluent. The percent of CD56 cells was about the same whether the Quick Spin was used or the hollow fiber membrane apparatus was used. Signal-to-noise ratios were greatly improved over the no wash control, no matter which washing protocol was used. Washing the sample two times with the hollow fiber membrane apparatus produced the best signal-to noise ratio.

In similar experiments, for unwashed samples the average percent of debris was 10.3% and the average signal to noise ratio was 11.4. As defined herein, debris means events falling below threshold measurement values. In comparison, using the hollow fiber membrane apparatus, the average percent of debris was 2.5%, which means that greater than 75% of the original 10.3% of debris was removed. In addition, the average signal to noise ratio was 23.8, which means that there was greater than a 200% improvement in the signal to noise ratio. Using the Quick Spin protocol, the average percent debris was 2.6% and the average signal to noise ratio was 38.7. In other experiments, when cell samples were washed 2 or 3 times with the hollow fiber membrane apparatus ore interferants were removed and the signal to noise ratio further improved.

EXAMPLE 4

Evaluation of Cell Recovery

Figure 8:
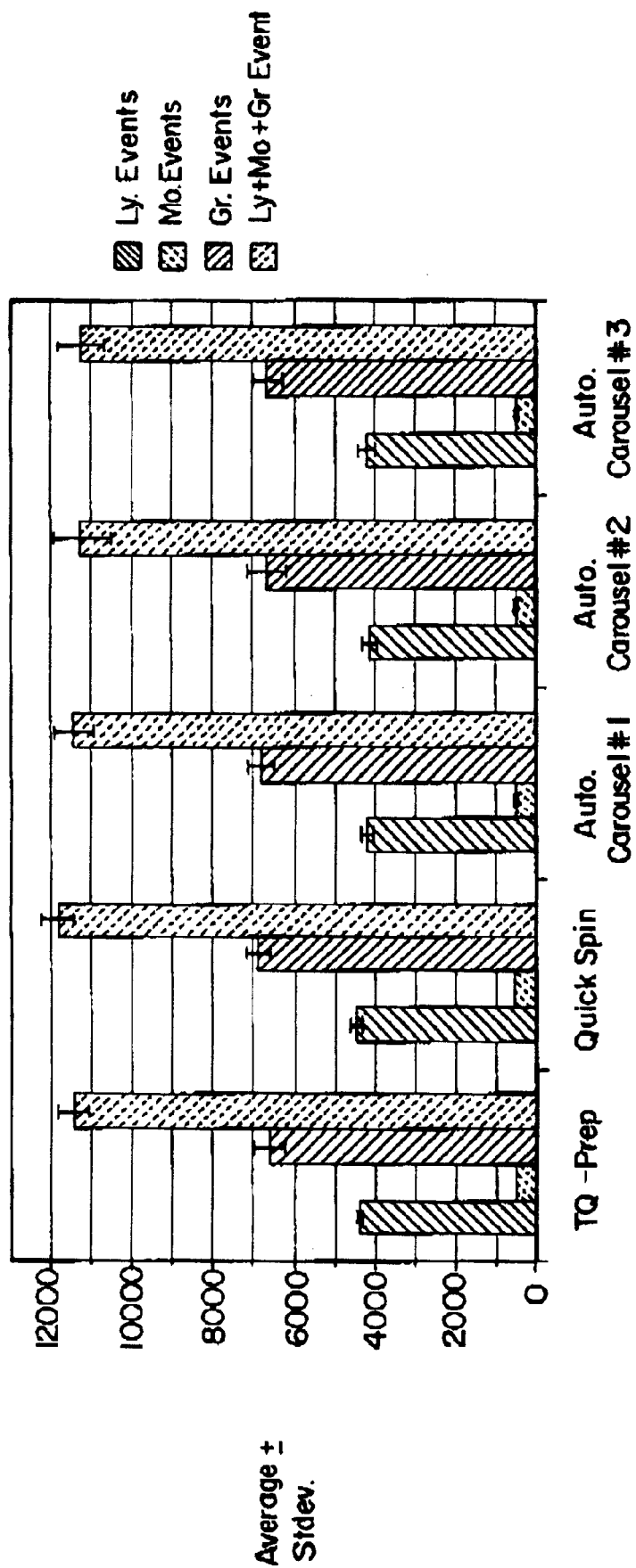
FIG. 8 is a graph showing data obtained from flow cytometric analysis of cell recovery from erythrocyte-lysed and fixed blood cell samples subject to different washing protocols. Data from lymphocyte ("Ly.") fractions, monocyte ("Mo.") fractions, granulocyte ("Gr.") fractions, and a combination of all three fractions are shown. Fractions were selected based on light scatter. Data are shown as averages with error bars indicating standard deviations.

Samples of whole human blood were processed, and washed according to the protocols described in Example 2, and then subjected to flow cytometric analysis using an EPICS XL flow cytometer according to the manufacturer's instructions. As shown in FIG. 8, results for cell recovery (number of indicated type of cells recovered from 100 microliter sample of whole blood after processing) show that little or no cell loss occurs in either the lymphocyte, monocyte, granulocyte (cell type determined by light scatter) fractions of the samples. Moreover, cell recovery using the apparatus of Example I was about equivalent to that obtained using the Quick Spin protocol. "TQ-Prep" samples (n=5) were not washed; "Quick Spin" samples (n=5) were washed according to the Quick Spin protocol described herein. "Auto" samples (n=32) were washed one time using a hollow fiber membrane apparatus.

EXAMPLE 5

Accuracy

Figure 9:
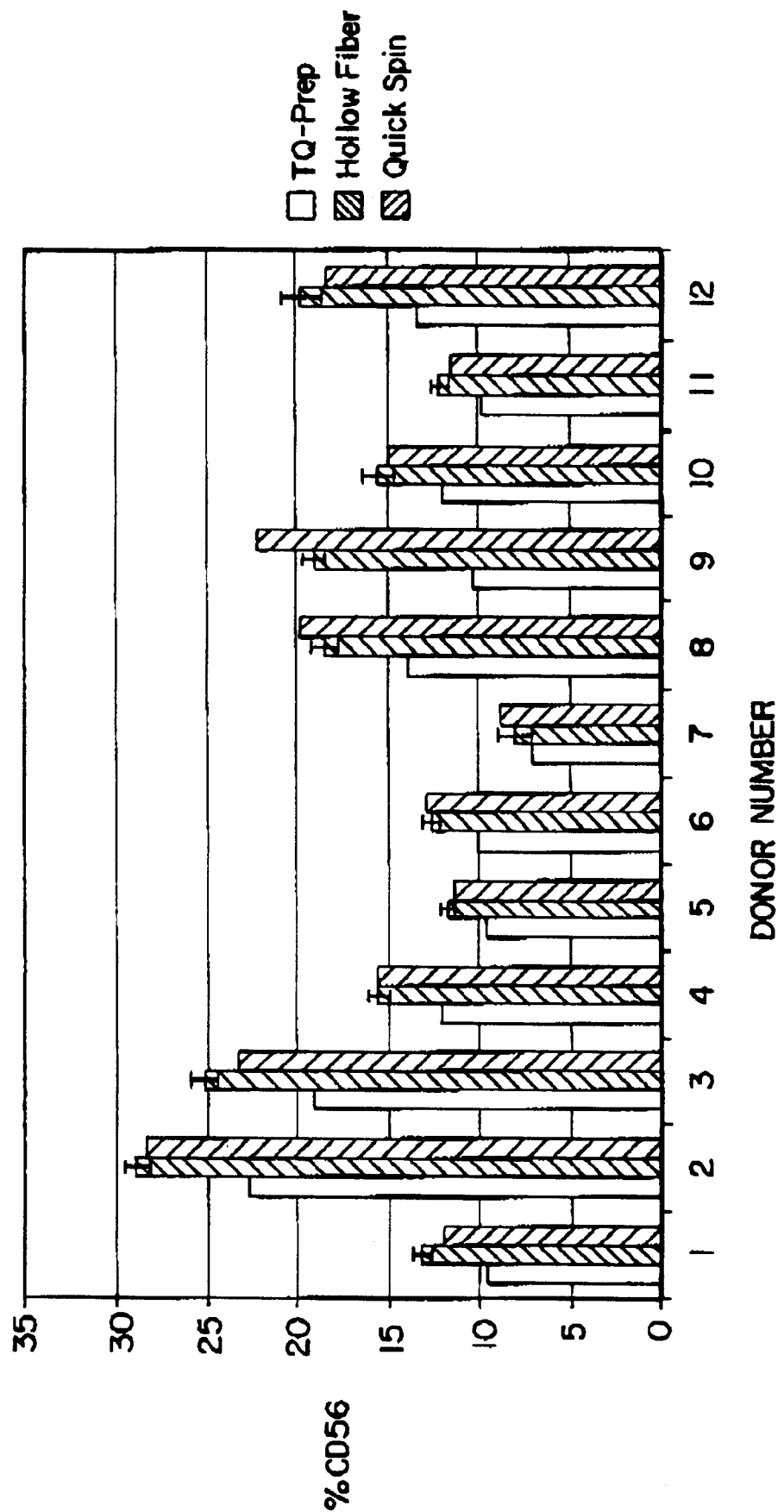
FIG. 9 is a graph showing data obtained from flow cytometric analysis of blood cell samples taken from 12 donors and stained for CD56, erythrocytelysed, and fixed. Data are presented as percent CD56$^+$, and are shown as averages of two to twelve replicates per donor. Error bars indicate standard deviation.

Samples of whole human blood from several different donors were stained for CD56, processed, and washed according to the protocols described in Example 2. "TQ-Prep" samples were not washed; "Quick Spin" samples were washed according to the Quick Spin protocol described herein; and "Hollow Fiber" samples were washed one time using a hollow fiber membrane apparatus. The samples were then subjected to flow cytometric analysis using an EPICS XL flow cytometer according to the manufacturer's instructions. As shown in FIG. 9, the percentage of cells that were CD56+ varied from donor to donor but, for any one donor, was about the same whether the Quick Spin was used or the hollow fiber membrane apparatus was used.

EXAMPLE 6

Precision

Thirty-two aliquots of one sample of whole human blood were stained for CD56, processed, and washed according to the protocols described in Example 2, and then subjected to flow cytometric analysis using a COULTER EPICS XL flow cytometer according to the manufacturer's instructions to determine the percent of CD56+ cells in each aliquot. The average percent of CD56+ cells among the aliquots was 17.44% with a standard deviation of 0.74 and a coefficient of variation of 4.27%. In a similar experiment using 28 aliquots, the average percent of CD56+ cells among the aliquots was 15.6% with a standard deviation of 0.6 and a coefficient of variation of 3.5%.

EXAMPLE 7

Cell Carryover

Figure 10:
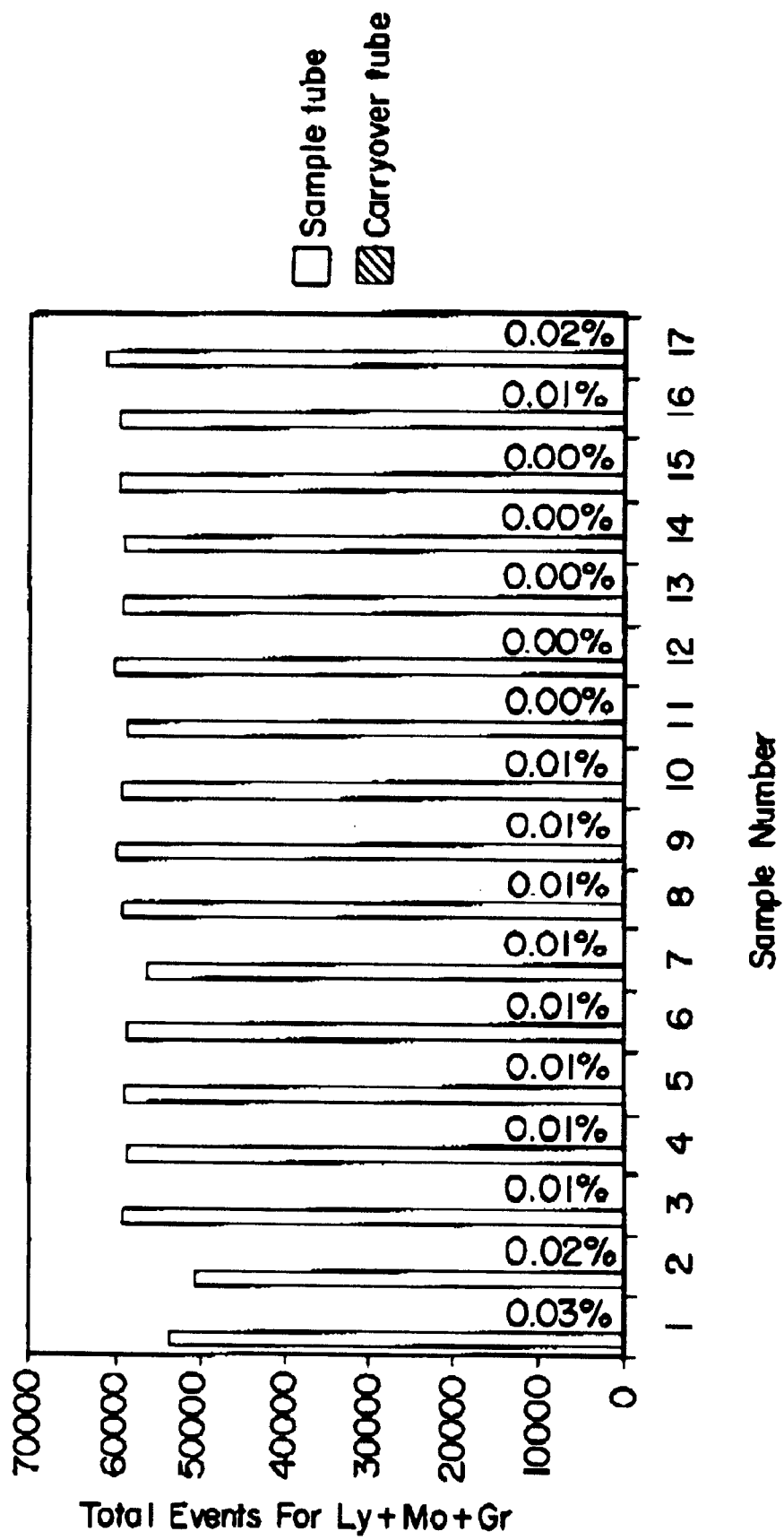
FIG. 10 is a graph showing the amount of cell carryover from concentrated cell samples washed with a hollow fiber membrane apparatus. After washing the cell sample and then cleaning the hollow fiber membrane, blank sample tubes were "washed" using the same hollow fiber membrane. The number of cells carried over from the cell sample to the blank sample tube were quantified using flow cytometry. Data are shown as percent of cells from cell sample carried over to blank sample. Seventeen samples from one donor were tested. The percent of carryover cells from the original total number of events is 0.03% or less. Consequently, FIG. 10 does not show a bar for the number of cells that were carry overed.

Whole blood cell samples were processed as described in Example 2 and then concentrated to four times normal cell concentrations. Each sample was then washed using the apparatus of Example 1 (per the protocol of Example 2C with cleaning of the hollow fiber membrane after sample washing). The apparatus was then used to "wash" a blank sample containing only buffer without cells. The blank sample was analyzed for the presence of cells using a flow cytometer. As shown in FIG. 10, carryover of cells from test to test was very low, ranging from 0.00% to 0.03% of cells being carried over to subsequent analysis.

EXAMPLE 8

Other Applications

The apparatus and methodology of the invention are also suitable for other analyses not explicitly described in detail herein. Such other applications include protein analysis of urine. In addition, applications which have traditionally utilized centrifugation as part of their cellular analysis method are specifically envisioned for use with the disclosed hollow fiber membrane apparatus and method described herein. For example, many different cell populations have been analyzed using the apparatus. Additionally, many different probe types have been used in the invention. For instance, aside from erythrocyte-depleted whole blood samples, the hollow fiber membrane apparatus has been successfully used with cell lines, purified white blood cell subsets; erythrocytes; platelets; bone marrow cells; and cells in cerebrospinal, synovial, peritoneal, ascites, pleural, pericardial fluids and homogenized tissue. The erythrocyte agglutination techniques commonly practiced in the blood banking field for the typing of blood and for compatibility testing, which are traditionally centrifugation dependent, can be readily adapted for performance using the methodology and apparatus of the invention. Probes that have been successfully used in the invention include fluorescently labeled monoclonal antibodies that are specific for the cell surface antigens such as immunoglobulin, kappa and lambda factors, CD5, CD7, CD10, CD13, CD19, CD33, CD34, CD38, CD41, CD45, CD41, CD42b, CD61, CD63, CD64, CD71, and CD117; as well as intracellular antigens such as various types of hemoglobin. Various other antibody and non-antibody probes such as chemical and biologic constructs that bind to receptor molecules on the cell surface, enzymatic substrates which react with cellular enzymes within the cell, antibody and non-antibody probes which react with cytoplasmic antigens within the cell, DNA and RNA probes which react with nucleic acids sequences within the cells and various intracellular dyes that react with cytoplasmic and nuclear structures within the cell are expected to be compatible with the invention. It is thus envisioned that most types of cells and probes are compatible with the invention, especially if the selected cell type is larger and the selected probe is smaller than the pores of the selected hollow fiber membrane.

Figure 11:
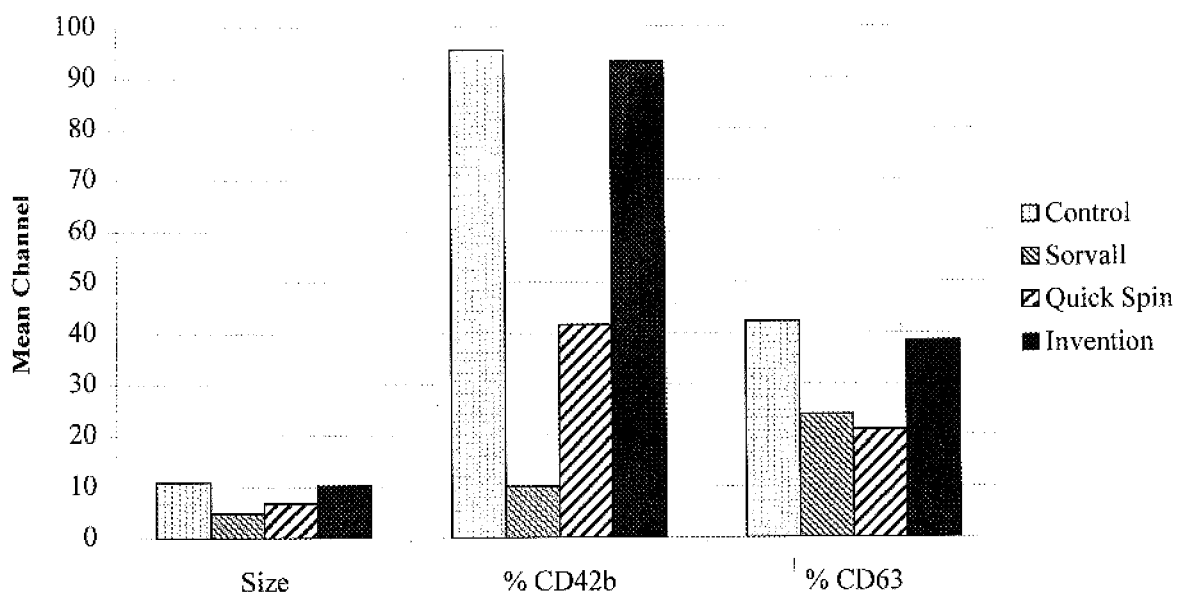
FIG. 11 is a graph showing data obtained from flow cytometric analysis of platelet samples stained for CD42b and CD63. 20 ul of anti-CD42b and 20 ul of anti-CD63 fluorescently-labeled antibodies were incubated with 100 ul of platelet rich plasma (after gravity sedimentation) for 10 minutes without shaking or mixing. "Control" samples were not washed; "Sorvall" samples were washed in a SORVALL® Cellwasher 2 (E.I. du Pont de Nemours) using the AUTO mode per the manufacturers instructions; "Quick Spin" samples were washed according to the Quick Spin protocol described herein; and "Invention" samples were washed one time using a hollow fiber membrane apparatus. Data were obtained using a COULTER® EPICS® XL™ flow cytometer (Beckman Coulter Inc., Miami, Fla.) and presented as size (determined based on forward and orthogonal light scatter), percent CD42b (mean channel fluorescence), and percent CD63 (mean channel fluorescence). Data shown are averages of three replicates using one donor.
Figure 12:
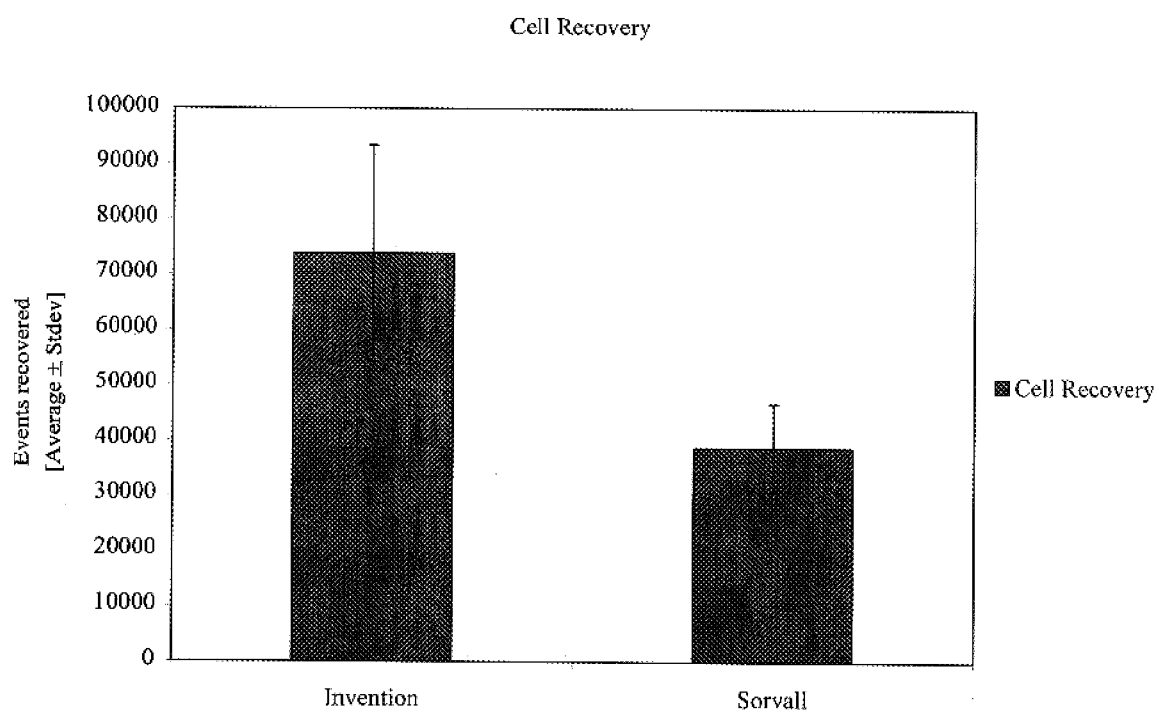
FIG. 12 is a graph showing data obtained from flow cytometric analysis of bone marrow cell samples stained for CD56, erythrocyte-lysed, and fixed using a TQ-Prep™ apparatus (Beckman Coulter, Inc., Miami, Fla.). "Sorvall" samples were washed in a SORVALL® Cellwasher 2 using the AUTO mode per the manufacturers instructions, and "Invention" samples were washed one time using a hollow fiber membrane apparatus. Data were obtained using an EPICS XL flow cytometer and are presented as cell recovery (number of event in a thirty second run) and signal-to-noise ratio (as described herein). Data shown are averages of three donors with one replicate per donor. Error bars represent standard deviation.
Figure 13:
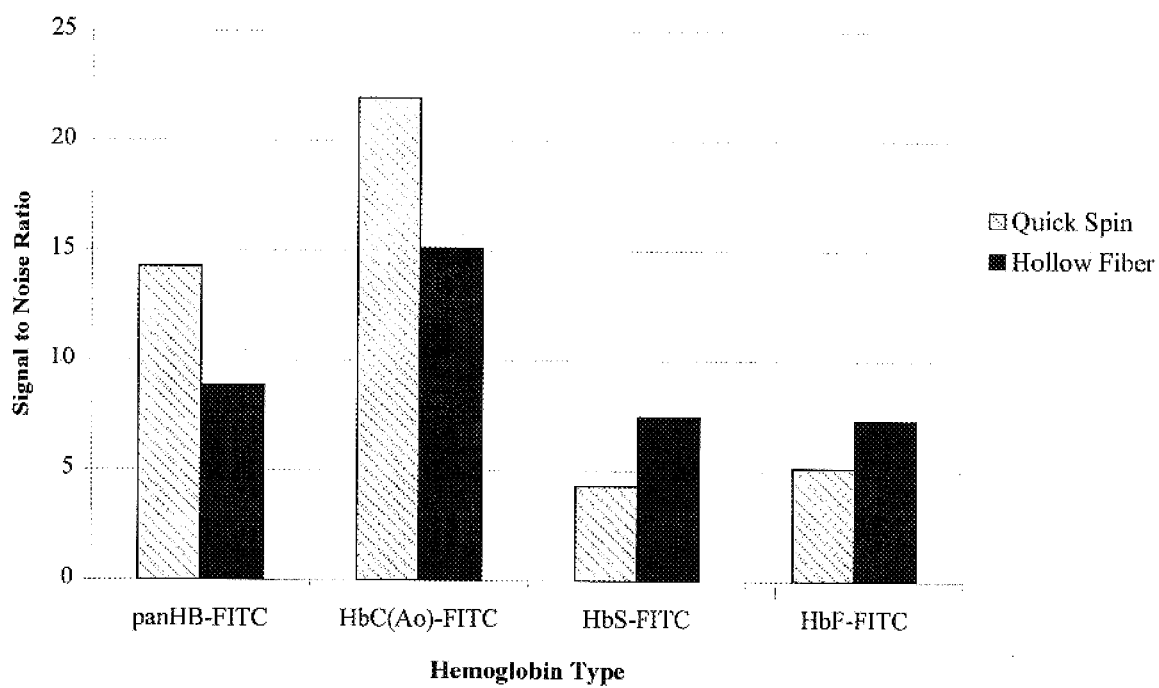
FIG. 13 is a graph showing data obtained from flow cytometric analysis of blood cell samples stained for hemoglobin. 200 ul of whole blood were cross-linked, permeabilized, and stabilized using commercially available reagents according to standard protocols. 20 ul of the prepared permeabilized RBCs were stained with the following amounts of individual antibodies: MsIgG1-PE/MsIgG1-FITC-20 ul, PanHb-FITC-10 ul, HbC-FITC-30 ul (cross reactive with HbAo), HbS-FITC-30 ul, HbF-FITC-30 ul, or HbA1c-FITC-10 ul; mixed for 20 min; and then washed. "Quick Spin" samples were washed according to the Quick Spin protocol described herein; and "Invention" samples were washed one time using a hollow fiber membrane apparatus. Data were obtained using an EPICS XL flow cytometer and are presented as signal-to-noise ratios (as described herein). Data shown are based on one replicate per test condition.

For example, referring to FIG. 11, application of the invention to platelet samples is shown by flow cytometric analysis of platelet samples stained for CD42b and CD63. Additionally, as another example, referring to FIG. 12, application of the invention to bone marrow samples is shown by flow cytometric analysis of bone marrow cell samples stained for CD56. Cell recovery and signal-to-noise ratio were comparable between "Invention" which is the apparatus and method described herein and the Sorvall apparatus and washing method. Referring now to FIG. 13, application of the invention for intracellular analysis is shown by flow cytometric analysis of permeabilized blood cell samples stained for hemoglobin. Signal-to-noise ratios were comparable between "Hollow Fiber" which is the apparatus and method described herein and Quick Spin washing method described in Example 2.

EXAMPLE 9

Cell Washing Apparatus Integrated With a Cell Analyzer

It is specifically envisioned that the cell washing apparatus of the invention can be integrated with one or more conventional cell analyzers thereby obviating a manual step of transferring a sample of washed cells from the washing device to the analyzer. For example, the cell washing apparatus described herein could be integrated with a flow cytometer such as a COULTER EPICS® brand flow cytometer by providing robotic means for transferring a test tube from a cell sample washed using the cell washing apparatus of the invention such that the tube becomes positioned so that it can be analyzed in the flow cytometer. As one example, a conveyor could transport a carousel containing several washed samples from a position suitable for washing the cells (e.g., proximal to the cell washing device) to another position suitable for analyzing the samples (e.g., proximal to the flow cytometer). Fluid connections and conduits would aspirate washed cell samples into the flow cytometer for analysis.

Alternatively, the cell washing apparatus of the invention can be integrated with one or more hematology instruments. In this embodiment, the blood cell sample would be washed after lysing the erythrocytes to remove remaining cellular debris. Still further, the blood cell sample could be washed prior to any biological or chemical reaction with the blood cell sample so that interferants are removed from the blood cell sample.

While the above specification contains many specifics, these should not be construed as limitations on the scope of the invention, but rather as examples of preferred embodiments thereof. Many other variations are possible. For example, the invention includes an apparatus for removing interferants from a cell sample that has only one hydraulic force transducer rather than two pumps and a vacuum source. The various hoses and valves within this apparatus can be connected in a manner to cooperate with the sole hydraulic force transducer, so that the apparatus functions much as the described preferred embodiments. As another example, a method of concentrating a cell sample by removing liquid from the sample using a microporous hollow fiber membrane is included within the invention. Accordingly, the scope of the invention should be determined not by the embodiments illustrated, but by the appended claims and their legal equivalents.

What is claimed is:

1. An apparatus for automatically removing interferants from a sample of cells containing cells of interest and interferants, the apparatus comprising:
   a) a vacuum source,
   b) a filtration device comprising:
      i. an impermeable housing that forms an extramembrane chamber, wherein said housing contains at least three ports and wherein at least one port is connected by a conduit to the vacuum source; and
      ii. a filter in said chamber that selectively retains cells of interest while allowing interferants to pass through the filter, said filter comprising a microporous hollow fiber membrane having a plurality of pores, wherein the microporous hollow fiber membrane is fashioned into at least one tube defining a lumen, said tube having a first opening at one end of the tube, and a second opening at the opposite end of the tube,
   c) a sample transporting conduit from one of said ports in said housing through which a cell sample passes from a sample container into the filtration device by operation of said vacuum source, wherein the first opening of said tube of said filter is fluidly connected to the sample transporting conduit such that the sample of cells can be moved from the cell sample container through the first opening into the lumen; and
   d) a buffer transporting conduit from one of said ports in said housing which fluidly connects to a buffer reservoir, which provides a means for buffer to enter into said filtration device to recover the retained cells through one of said ports, wherein the second opening of said tube of said filter is fluidly connected to the buffer transporting conduit such that the buffer can be moved from the buffer reservoir through the second opening into the lumen.

2. The apparatus of claim 1, wherein the port in said housing which fluidly connects to a buffer reservoir is different from the port in said housing which is adapted to aspirate a cell sample from a sample container into the filtration device by said vacuum source.

3. The apparatus of claim 1, wherein a controller operatively coupled to said sample transporting conduit enables recovery of the retained cells from said filtration device through said sample transporting conduit.

4. The apparatus of claim 3, wherein said controller operatively coupled to said sample transporting conduit enables the recovery of the retained cells to be directed into the sample container from which the cell simple has been aspirated.

5. The apparatus of claim 1, wherein the pores have a diameter of approximately 0.1 microns to about 5 microns.

6. The apparatus of claim 1, wherein the pores have a diameter of approximately 0.2 microns to about 2 microns.

7. The apparatus of claim 1, wherein said vacuum source is fluidly connected to the extramembrane chamber such that application of a vacuum from the vacuum source to the extramembrane chamber causes the sample of cells to be aspirated from a cell sample container through the sample transporting conduit into the filtration device, and interferants contained in the sample of cells to flow through the filter into the extramembrane chamber and exit through a waste transporting conduit.

8. The apparatus of claim 7, further comprising at least one pump and a plurality of valves, the at least one pump providing an hydraulic force for transporting a buffer contained within said buffer reservoir into the filtration device, and a detergent solution contained within a detergent solution reservoir into the filtration device; and the plurality of valves being adapted to open and close such that the vacuum from the vacuum source can be applied to the extramembrane chamber such that the buffer, the detergent solution, and interferants contained in the sample of cells within the filtration device can be controllably removed from the filtration device; and the hydraulic force provided from the at least one pump can be directed to transport the buffer from the buffer reservoir to the filtration device, and the buffer from the buffer reservoir to the cell sample container, and the detergent solution from the detergent solution reservoir to filtration device.

9. The apparatus of claim 8, further comprising a computer controller for controlling the at least one pump and the plurality of valves.

10. The apparatus of claim 1, wherein one of the ports is fluidly connected to a detergent solution reservoir adapted for containing a detergent solution.

11. The apparatus of claim 1, further comprising a conduit which is fluidly connected to a cell analyzer.

12. The apparatus of claim 11, wherein the cell analyzer measures fluorescence.

13. The apparatus of claim 11, wherein the cell analyzer is a flow cytometer.

14. The apparatus according to claim 1, further comprising:
   a first waste transporting conduit from one of said ports which opens directly into said extramembrane chamber through which is transported, by the application of a vacuum force, said interferants from the filter to said vacuum source; and
   a second waste transporting conduit, through which is transported said interferants from the vacuum source to a waste unit.

* * * * *